United States Patent [19]

Shapiro

[11] Patent Number: 4,904,299

[45] Date of Patent: Feb. 27, 1990

[54] HERBICIDAL N-HYDROXY-N'-SULFONYLGUANIDINES

[75] Inventor: Rafael Shapiro, Wilmington, Del.

[73] Assignee: E. I. Du Pont de Nemours and Co., Wilmington, Del.

[21] Appl. No.: 156,891

[22] Filed: Feb. 17, 1988

Related U.S. Application Data

[60] Division of Ser. No. 60,212, Jun. 10, 1987, Pat. No. 4,750,930, which is a division of Ser. No. 736,950, May 22, 1985, Pat. No. 4,689,070, which is a continuation-in-part of Ser. No. 551,381, Nov. 17, 1983, abandoned, which is a continuation-in-part of Ser. No. 455,504, Jan. 4, 1983, abandoned.

[51] Int. Cl.$^4$ ............... C07D 239/42; C07D 401/12; C07D 409/12; A01N 43/54
[52] U.S. Cl. .............................. 71/92; 71/90; 71/91; 544/49; 544/320; 544/321; 544/324; 544/331; 544/332; 544/323
[58] Field of Search ................ 71/92, 90, 91; 544/49, 544/324, 323

[56] References Cited

U.S. PATENT DOCUMENTS

| | | | |
|---|---|---|---|
| 4,310,346 | 1/1982 | Levitt et al. | 544/208 |
| 4,544,401 | 10/1985 | Levitt | 71/92 |
| 4,559,079 | 12/1985 | Shiokawa | 71/92 |
| 4,568,381 | 2/1986 | Saito | 71/92 |
| 4,602,938 | 7/1986 | Moriya | 71/92 |
| 4,721,785 | 1/1988 | Moriya et al. | 71/92 |
| 4,725,303 | 2/1988 | Moriya et al. | 544/320 |

FOREIGN PATENT DOCUMENTS 027482 4/1981 European Pat. Off. .
79/2657 6/1980 South Africa .

OTHER PUBLICATIONS

Abstract of South African Pat. No. 79/2657, published May 2, 1980.

Primary Examiner—John M. Ford

[57] ABSTRACT

Novel N-hydroxy-N'-sulfonylguanidine compounds are described which possess significant herbicidal and plant growth regulant activity for control of undesired vegetation.

4 Claims, No Drawings

HERBICIDAL N-HYDROXY-N'-SULFONYLGUANIDINES

This application is a divisional of my copending application Ser. No. 060,212, filed Jun. 10, 1987, now U.S. Pat. No. 4,750,930, which is a divisional of Ser. No. 736,950, filed May 22, 1985, now issued as U.S. Pat. No. 4,689,070, which is a continuation-in-part of Ser. No. 551,381, filed Nov. 17, 1983, now abandoned, which is a continuation-in-part of Ser. No. 455,504, filed Jan. 4, 1983, now abandoned.

BACKGROUND OF THE INVENTION

This invention relates to certain novel N-hydroxy-N'-sulfonylguanidine compounds, to compositions containing such compounds, and to a method of use of such compositions to control the growth of undesired vegetation.

U.S. Pat. No. 4,127,405 issued Nov. 28, 1978 discloses substituted triazinyl arylsulfonylurea compounds of the following formula:

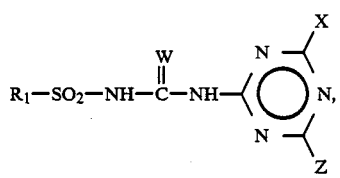

while U.S. Pat. No. 4,169,719 issued Oct. 2, 1979 discloses substituted pyrimidinyl arylsulfonylurea compounds of the following formula:

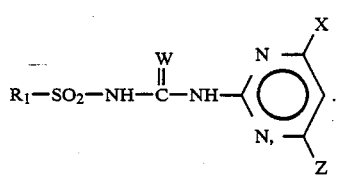

The triazine and pyrimidine compounds within the scope of the '405 and '719 patents include those wherein W can be oxygen or sulfur.

U.S. Pat. No. 4,310,346 issued Jan. 12, 1982 discloses sulfonylisothiourea compounds of the formula

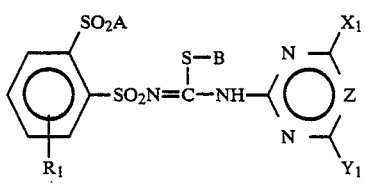

wherein
B is $C_1-C_6$ alkyl, $CH_2CH_2OCH_3$, $CH_2CH_2OCH_2CH_3$, $CH_2CH_2CH_2OCH_3$, $CH_2Q$,

where Q is $CO_2-C_{1-3}$ alkyl,

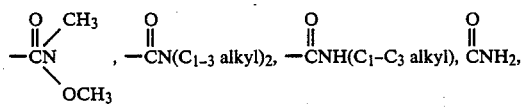

phenyl, phenyl substituted with chlorine, CN, $C_{2-4}$ alkenyl, $C_{2-4}$ alkynyl, $OR_{11}$, where $R_{11}$ is $C_1-C_4$ alkyl, $-CH_2OCH_2CH_2OCH_3$ or $-CH_2OCH_2CH_2OCH_2CH_3$.

South African Pat. No. 79/2657, published Jun. 30, 1980 discloses sulfonylisothiourea compounds of the formula

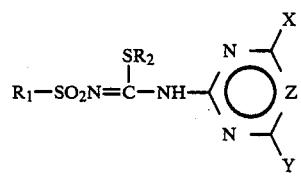

wherein
$R_2$ is $C_1-C_{20}$ alkyl; $CH_2CH_2OCH_3$; $CH_2CH_2OCH_2CH_3$; $CH_2CH_2CH_2OCH_3$; $CH_2OA'$ where $A'$ is $C_1-C_{12}$ alkyl, $-CH_2CH_2OCH_3$, $-CH_2CH_2OCH_2CH_3$, phenyl or phenyl substituted with 1-2 $NO_2$, 1-2 Cl, or 1-2 $CH_3$; $CH_2A$,

where A is $CO_2(H, C_1-C_4$ alkyl),

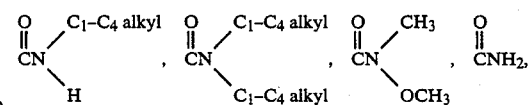

phenyl, CN, $C_2-C_4$ alkenyl, $C_1-C_4$ alkynyl, phenyl substituted with 1-2 $CH_3$, 1-2 $NO_2$, 1-2 $OCH_3$, 1-2 chlorine or phenoxy.

U.S. Pat. No. 4,301,286 issued Nov. 17, 1981 discloses O-alkylsulfonylisoureas of the formula

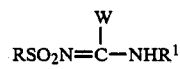

wherein
W is Cl, Br or $OR^{12}$; and
$R^{12}$ is $C_1-C_{12}$ alkyl, $C_3-C_4$ alkenyl, $CH_2CH_2OCH_3$, $CH_2CH_2OCH_2CH_3$, $(CH_2)_3OCH_3$, benzyl, $CHR^{13}CO_2R^{14}$, where $R^{13}$ is H or $CH_3$ and $R^{14}$ is $C_1-C_4$ alkyl.

South African patent application No. 84/4808 discloses herbicidal sulfonamides of formula

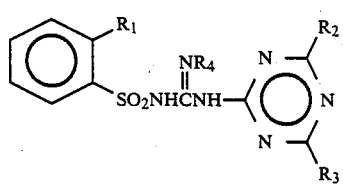

wherein
R₁ is a phenyl or phenoxy group; each of
R₂ and R₃ is a lower alkyl or lower alkoxy group; and
R₄ is a hydrogen atom, a lower alkyl group or a lower alkoxy group.

The compounds taught in the above references are useful as general or selective herbicides having both preemergent and postemergent herbicidal activity or plant growth regulant activity.

SUMMARY OF THE INVENTION

The novel sulfonylguanidine compounds of the present invention incorporating a guanidyloxyl moiety are highly active herbicides in both preemergent and postemergent applications. Certain compounds additionally exhibit selective herbicidal safety to wheat and barley. Specifically, the invention relates to novel compounds of formula I, agriculturally suitable compositions containing them and their method-of-use as pre-emergent and/or post-emergent herbicides or plant growth regulants.

$$L-SO_2NHCN-A \overset{\overset{N-R'}{\|}}{\underset{R}{}} \quad I$$

wherein
R is H or CH₃;
R' is OH, OC(O)R₁, OC(O)NR₂R₃, OCOR₄, OR₃ or R₃;
R₁ is C₁–C₃ alkyl or CF₃;
R₂ is H, CH₃ or C₂H₅;
R₃ is C₁–C₃ alkyl;
R₄ is C₁–C₃ alkyl;
L is

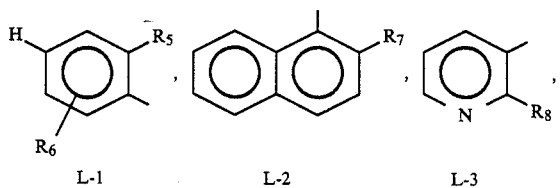

L-1, L-2, L-3

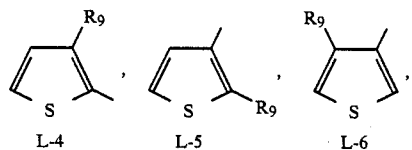

L-4, L-5, L-6

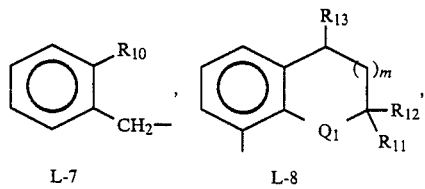

L-7, L-8

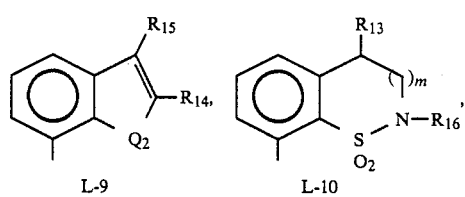

L-9, L-10

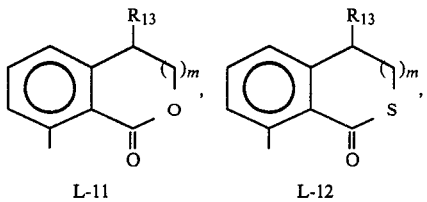

L-11, L-12

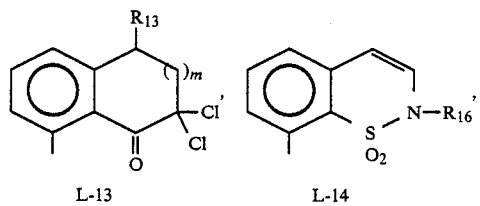

L-13, L-14

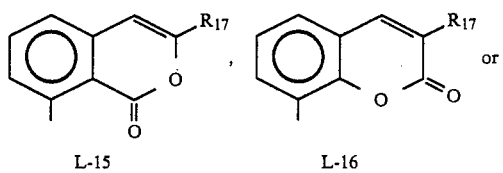

L-15, L-16

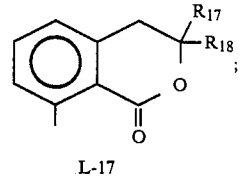

L-17

R₅ is C₁–C₄ alkyl, C₁–C₄ alkoxy, OCH₂CH₂OCH₃, F, Cl, Br, NO₂, CF₃, CO₂R₁₉, SO₂NR₂₀R₂₁, SO₂N(OCH₃)CH₃, OSO₂R₂₂, S(O)ₙR₂₃, WCF₃, WCHF₂, C₃–C₄ alkenyloxy, C₃–C₄ alkynyloxy, C₁–C₂ alkyl substituted with OCH₃ or OCH₂CH₃, C₆H₅,

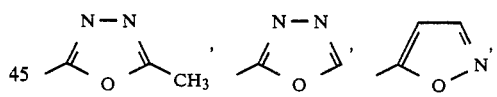

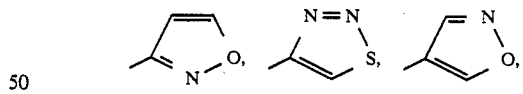

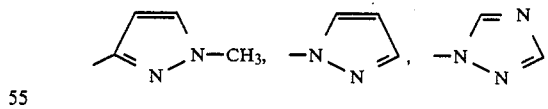

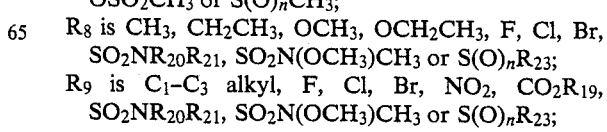

R₆ is H, F, Cl, Br, CF₃, CH₃, OCH₃, SCH₃ or OCF₂H;
R₇ is H, CH₃, OCH₃, F, Cl, Br, SO₂N(CH₃)₂, OSO₂CH₃ or S(O)ₙCH₃;
R₈ is CH₃, CH₂CH₃, OCH₃, OCH₂CH₃, F, Cl, Br, SO₂NR₂₀R₂₁, SO₂N(OCH₃)CH₃ or S(O)ₙR₂₃;
R₉ is C₁–C₃ alkyl, F, Cl, Br, NO₂, CO₂R₁₉, SO₂NR₂₀R₂₁, SO₂N(OCH₃)CH₃ or S(O)ₙR₂₃;

$R_{10}$ is Cl, $NO_2$, $CO_2CH_3$, $CO_2CH_2CH_3$, $SO_2N(CH_3)_2$, $OSO_2CH_3$, $SO_2CH_3$, $SO_2CH_2CH_3$, $OCH_3$ or $OCH_2CH_3$;
$R_{11}$ is H, $CH_3$ or $CH_2CH_3$;
$R_{12}$ is H, $CH_3$ or $CH_2CH_3$;
$R_{13}$ is H or $CH_3$;
$R_{14}$ is H or $CH_3$;
$R_{15}$ is H or $CH_3$;
$R_{16}$ is $CH_3$ or $CH_2CH_3$;
$R_{17}$ is H or $C_1$-$C_4$ alkyl;
$R_{18}$ is H or $CH_3$;
$R_{19}$ is $C_1$-$C_4$ alkyl, $CH_2CH_2OCH_3$, $CH_2CH_2Cl$ or $CH_2CH=CH_2$;
$R_{20}$ is $C_1$-$C_3$ alkyl;
$R_{21}$ is $C_1$-$C_3$ alkyl;
$R_{22}$ is $C_1$-$C_3$ alkyl or $N(CH_3)_2$;
$R_{23}$ is $C_1$-$C_3$ alkyl or $CH_2CH=CH_2$;
m is 0 or 1;
n is 0 or 2;
$Q_1$ is O, S, $SO_2$ or $NR_{17}$;
$Q_2$ is O, S or $NR_{17}$; and
W is O, S or $SO_2$;
A is

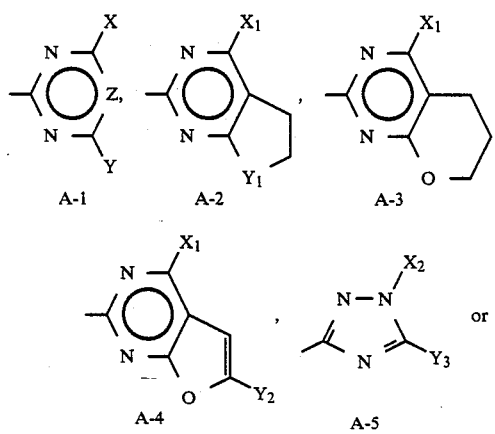

X is $CH_3$, $OCH_3$, $OCH_2CH_3$, Cl, F, Br, $OCF_2H$, $CH_2F$ or $CF_3$;
Y is H, $CH_3$, $OCH_3$, $OCH_2CH_3$, $CH_2OCH_3$, $CH_2OCH_2CH_3$, $N(CH_3)_2$, $CH_2CH_3$, $CF_3$, $SCH_3$, $OCH_2CH=CH_2$, $OCH_2C\equiv CH$, $OCH_2CF_3$, $OCH_2CH_2OCH_3$, $CH_2SCH_3$, $OCF_2H$, $SCF_2H$, $CR_{24}(QCH_3)_2$,

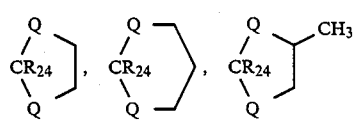

or $CR_{24}(QCH_2CH_3)_2$;
Q is O or S;
$R_{24}$ is H or $CH_3$;

Z is CH or N;
$Y_1$ is $CH_2$ or O;
$X_1$ is $CH_3$, $OCH_3$, $OCH_2CH_3$ or $OCF_2H$;
$Y_2$ is H or $CH_3$;
$X_2$ is $CH_3$, $CH_2CH_3$ or $CH_2CF_3$;
$Y_3$ is $OCH_3$, $OCH_2CH_3$, $SCH_3$, $CH_3$ or $CH_2CH_3$;
$X_3$ is $CH_3$ or $OCH_3$;
provided that
(1) the total number of carbon atoms of $R_{20}$ and $R_{21}$ is less than or equal to four;
(2) when m is 1, then $R_{13}$ is H;
(3) when L is L-17, then $R_{17}$ and $R_{18}$ are not simultaneously H;
(4) when X is Cl, F or Br, then Z is CH and Y is $OCH_3$, $OCH_2CH_3$, $N(CH_3)_2$ or $OCF_2H$;
(5) when R' is $C_1$-$C_3$ alkoxy or $C_1$-$C_3$ alkyl, and L is L-1 then either $R_5$ is other than $C_6H_5$ or $R_6$ is other than H; and
(6) when X or Y is $OCF_2H$, then Z is CH.

This invention also relates to novel compounds of Formula II, suitable agricultural compositions containing them and their method of use as general or selective preemergent or postemergent herbicides or plant growth regulants.

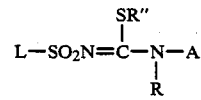

wherein
R" is $C_1$-$C_3$ alkyl;
R, L and A are defined for Formula I;
provided that
(1) when L is L-1 and A is A-1, $R_5$ is $C_2$-$C_4$ alkyl, $C_2$-$C_4$ alkoxy, $OCH_2CH_2OCH_3$, $OSO_2R_{22}$, $S(O)_nCH_2CH=CH_2$, $WCF_2$, $WCHF_2$, $C_3$-$C_4$ alkenyloxy, $C_3$-$C_4$ alkynyloxy, $C_1$-$C_2$ alkyl substituted with $OCH_3$ or $OCH_2CH_3$, $C_6H_5$,

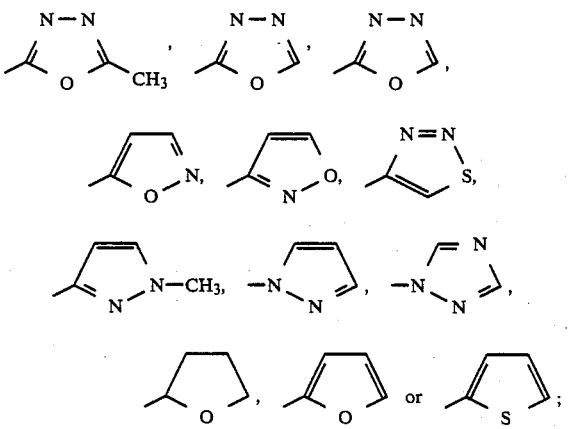

(2) when L is L-1 and A is A-2 or A-3, then $R_5$ is $C_2$-$C_4$ alkyl, $C_2$-$C_4$ alkoxy, $OCH_2CH_2OCH_3$, $OSO_2R_{22}$, $WCF_3$, $WCHF_2$, $C_3$-$C_4$ alkenyloxy, $C_3$-$C_4$ alkynyloxy, $C_1$-$C_2$ alkyl substituted with $OCH_3$ or $OCH_2CH_3$, $C_6H_5$,

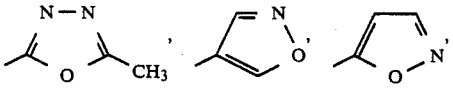

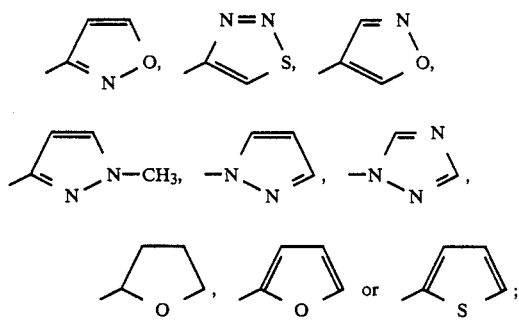

(3) when L is L-3 and A is A-1, A-2 or A-3, then $R_8$ is $SO_2NR_{20}R_{21}$, $SO_2N(OCH_3)CH_3$ or $SO_2R_{23}$;

(4) when L is L-4, L-5 or L-6 and A is A-1, A-2 and A-3, then $R_9$ is $C_1$-$C_3$ alkyl, F, Cl, Br, $NO_2$, $SO_2NR_{20}R_{21}$, $SO_2N(OCH_3)CH_3$ or $S(O)_nR_{23}$; and (5) when L is L-2, then A is A-5 or A-6.

Preferred for reasons of their higher herbicidal activity, greater plant growth regulant activity or more favorable ease of synthesis are:

(1) Compounds of Formula I where R is H, R' is OH and A is A-1.

(2) Compounds of Formula I where R is H, R' is $C_1$-$C_2$ alkoxy and A is A-1.

(3) Compounds of Preferred 1 where Y is $CH_3$, $OCH_3$, $OCH_2CH_3$, $CH_2OCH_3$, $OCH_2CF_3$ or $CH(OCH_3)_2$ and X is $CH_3$, $OCH_3$, Cl or $CF_3$.

(4) Compounds of Preferred 2 where Y is $CH_3$, $OCH_3$, $OCH_2CH_3$, $CH_2OCH_3$, $OCH_2CF_3$ or $CH(OCH_3)_2$ and X is $CH_3$, $OCH_3$, Cl or $CF_3$.

(5) Compounds of Preferred 3 where L is L-1, L-2, L-3, L-5, L-8, L-10, L-11, L-16 or L-17.

(6) Compounds of Preferred 5 where L is L-1, $R_5$ is $OCH_3$, $OCH_2CH_3$, Cl, $NO_2$, $CF_3$, $CO_2CH_3$, $CO_2CH_2CH_3$, $SO_2N(CH_3)_2$, $SO_2N(OCH_3)CH_3$, $OSO_2R_{22}$, $S(O)_nR_{23}$, $OCF_2H$, $SCF_2H$, $C_6H_5$, $OCH_2CH=CH_2$, $OCH_2C\equiv CH$.

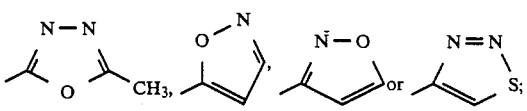

$R_{22}$ is $C_1$-$C_3$ alkyl;
$R_{23}$ is $CH_3$ and n is 2.

(7) Compounds of Preferred 4 where L is L-1, L-2, L-3, L-5, L-8, L-10, L-11, L-16 or L-17.

(8) Compounds of Preferred 7 where L is L-1, $R_5$ is $OCH_3$, $OCH_2CH_3$, Cl, $NO_2$, $CF_3$, $CO_2CH_3$, $CO_2CH_2CH_3$, $SO_2N(CH_3)_2$, $SO_2N(OCH_3)CH_3$, $OSO_2R_{22}$, $S(O)_nR_{23}$, $OCF_2H$, $SCF_2H$, $C_6H_5$, $OCH_2CH=CH_2$, $OCH_2C\equiv CH$,

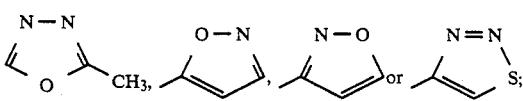

$R_{22}$ is $C_1$-$C_3$ alkyl;
$R_{23}$ is $CH_3$ and n is 2.

(9) Compounds of Preferred 5 where L is L-2 and $R_7$ is Cl, $CH_3$, $OCH_3$, $SCH_3$ or Br.

(10) Compounds of Preferred 5 where L is L-3 and $R_8$ is Cl, $SO_2CH_3$ or $SO_2N(CH_3)_2$.

(11) Compounds of Preferred 5 where L is L-5 and $R_9$ is $CO_2CH_3$ or $CO_2CH_2CH_3$.

(12) Compounds of Preferred 5 where L is L-8.

(13) Compounds of Preferred 5 where L is L-10.

(14) Compounds of Preferred 5 where L is L-11.

(15) Compounds of Preferred 5 where L is L-16.

(16) Compounds of Preferred 5 where L is L-17.

(17) Compounds of Preferred 7 where L is L-2 and $R_7$ is Cl, $CH_3$, $OCH_3$, $SCH_3$ or Br.

(18) Compounds of Preferred 7 where L is L-3 and $R_8$ is Cl, $SO_2CH_3$ or $SO_2N(CH_3)_2$.

(19) Compounds of Preferred 7 where L is L-5 and $R_9$ is $CO_2CH_3$ or $CO_2CH_2CH_3$.

(20) Compounds of Preferred 7 where L is L-8.

(21) Compounds of Preferred 7 where L is L-10.

(22) Compounds of Preferred 7 where L is L-11.

(23) Compounds of Preferred 7 where L is L-16.

(24) Compounds of Preferred 7 where L is L-17.

(25) Compounds of Formula II where R is H and A is A-1.

(26) Compounds of Preferred 25 where Y is $CH_3$, $OCH_3$, $OCH_2CH_3$, $CH_2OCH_3$, $OCH_2CF_3$ or $CH(OCH_3)_2$ and X is $CH_3$, $OCH_3$, Cl or $CF_3$;

(27) Compounds of Preferred 26 where L is L-1 and $R_5$ is $OSO_2R_{22}$, $SO_2CH_2CH=CH_2$, $OCF_2H$, $SCF_2H$, $OCH_2CH=CH_2$, $OCH_2C\equiv H$,

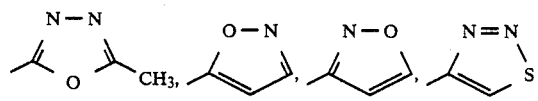

or $C_6H_5$.

Specifically Preferred for reasons of their highest herbicidal activity or greatest plant growth regulant activity or most favorable ease of synthesis are:

2-[[1-(4,6-dimethylpyrimidin-2-yl)amino]-1-(hydroxyimino)methyl]aminosulfonyl]benzoic acid methyl ester;

2-[[1-(4-methoxy-6-methylpyrimidin-2-yl)amino]-1-(hydroxyimino)methyl]aminosulfonyl]benzoic acid methyl ester;

N',N'-dimethyl-N-[[1-(4,6-dimethyl-1,3,5-triazin-2-yl)amino]-1-(hydroxyimino)methyl]-1,2-benzenedisulfonamide;

N',N'-dimethyl-N-[[1-(4-methoxy-6-methylpyrimidin-2-yl)amino]-1-(hydroxyimino)methyl]-1,2-benzenedisulfonamide;

3-chloro-N-[[1-(4,6-dimethoxypyrimidin-2-yl)amino]-1-[methoxyimino]methyl][1,1'-biphenyl]-2-sulfonamide;

N-[[1-(4,6-dimethoxy-1,3,5-triazin-2-yl)amino]-1-[methoxyimino]methyl]-3-methoxy[1,1'-biphenyl]-2-sulfonamide; and N-[[1-(4,6-dimethylpyrimidin-2-yl)amino]-1-(hydroxyimino)methyl]-2-chlorobenzenesulfonamide, m.p. 165-167.

DETAILED DESCRIPTION OF THE INVENTION

Synthesis

The compounds of Formula Ia may be prepared by the reaction of hydroxylamine with an appropriately substituted S-alkyl benzenesulfonyl isothiourea of Formula II, as shown in Equation 1.

Equation 1

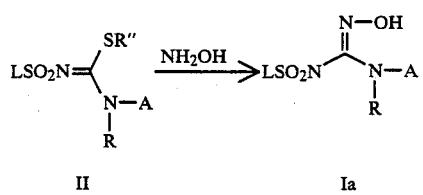

wherein

L, R, R" and A are as previously defined.

The reaction of Equation 1 is conducted by contacting 1-3 equivalents of hydroxylamine hydrochloride and an equivalent amount of sodium acetate with a compound of Formula II in a suitable solvent, such as tetrahydrofuran, at 0°-30° for 1-24 hours. The product may be isolated by removal of solvent and trituration of the residue with water.

The compounds of Formula II may be prepared by the methods described in U.S. Pat. No. 4,301,286 and are herein incorporated by reference. Alternatively, they may be prepared by the procedure outlined in Equation 2.

Equation 2

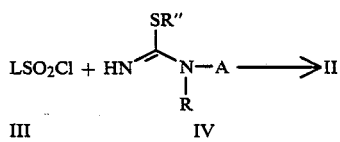

wherein

L, R, R" and A are as previously defined.

The reaction of Equation 2 may be carried out by contacting a sulfonyl chloride of Formula III with an appropriately substituted S-alkyl isothiourea of Formula IV in an inert solvent, such as methylene chloride or tetrahydrofuran, in the presence of an acid scavenger, such as aqueous sodium bicarbonate or a tertiary amine, such as triethylamine, for 1-3 days at 20°-40°. The product is isolated by removal of solvent and trituration of the residue with water, or by extraction from water with an organic solvent, concentration, and chromatography.

Reference to the following patents and patent applications is suggested for details regarding the preparation of the sulfonyl chlorides III: U.S. Pat. No. 4,169,719, U.S. Pat. No. 4,127,405; U.S. Pat. No. 4,383,113; U.S. Pat. No. 4,394,506; U.S. Pat. No. 4,120,691; U.S. Pat. No. 4,238,621; European patent application No. 80304286.0, published Jun. 10, 1981; European patent application No. 79302769.9, published Jul. 23, 1980; Canadian Pat. No. 1128042; European patent application No. 82301500.3, published Nov. 17, 1982; European patent application No. 81305160.4, published May 12, 1982; and copending U.S. patent application Ser. No. 410,993, filed Aug. 27, 1982; U.S. patent application Ser. No. 406,191, filed Aug. 11, 1982, U.S. patent application Ser. No. 499,443, filed May 31, 1983 and U.S. patent application Ser. No. 436,631, filed Oct. 10, 1982.

The preparation of the compounds of Formula IV is shown in Equations 3, 4 and 5.

Equation 3

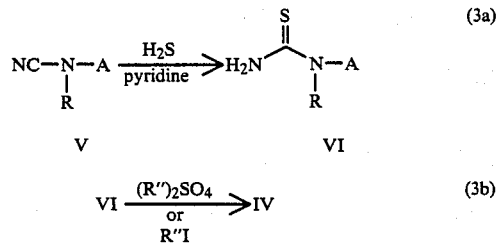

wherein

R, R" and A are as previously defined.

The reaction of Equation 3a may be carried out by saturation of a solution of a compound of Formula V in pyridine with hydrogen sulfide, allowing to react for 1 to 5 days at 25° to 40°, removal of pyridine in vacuo, and crystallization of the product with water or an organic solvent such as ether or methylene chloride. The resulting compound of Formula VI may be reacted according to Equation 3b with one equivalent of a dialkyl sulfate or alkyl iodide at 20° to 80° for 1 to 3 days to provide the corresponding alkyl sulfate or iodide salt of IV. The free base may be obtained by extraction from aqueous sodium bicarbonate with an organic solvent, such as ethyl acetate. An alternative synthesis of compounds of Formula VI is shown in Equation 4.

Equation 4

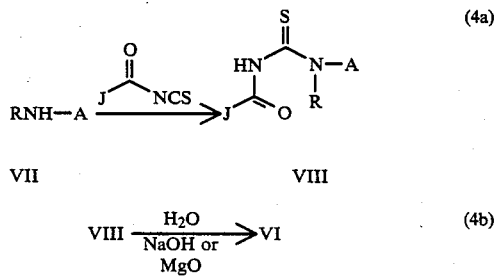

wherein

R and A are as previously defined; and J is $C_6H_5$ or $C_6H_5O$.

The reaction of Equation 4a is carried out by contacting a compound of Formula VII with 1-1.5 equivalents of benzoyl- or phenoxycarbonylisothiocyanate at 30°-80° for 1-24 hours in a suitable solvent, such as acetonitrile or tetrahydrofuran. The product may be isolated by cooling or concentration and filtration. The reaction of Equation 4b may be performed by heating the compound of Formula VIII in an aqueous medium, with or without a cosolvent, in the presence of 1 to 2 equivalents of an alkali metal hydroxide or an alkali earth oxide at 30° to 80° for 1-24 hours. The product is isolated by cooling, neutralization to pH 8, and filtration in the case where an alkali metal hydroxide is used, and in the case where an alkali earth oxide is used, the reaction mixture is filtered and the filtrate is concentrated, cooled, and filtered.

Heterocyclic amines of Formula VII and methods for preparing them are known in the art. The synthesis of heterocyclic amines such as those of Formula VII has been reviewed in "The Chemistry of Heterocyclic Compounds", a series published by Interscience Publ., N.Y. and London. 2-Aminopyrimidines are described by D. J. Brown in "The Pyrimidines", Vol. XVI of this series. 2-Amino-1,3,5-triazines can be prepared according to methods described by E. M. Smolin and L. Rapaport in "s-Triazines and Derivatives", Vol. XIII of the same series. The synthesis of triazines is also described by F. C. Schaefer, U.S. Pat. No. 3,154,547 and by K. R. Huffman and F. C. Schaefer; *J. Org. Chem.*, 28, 1816 (1963). See also U.S. patent application Ser. No. 434,038, filed Oct. 20, 1982, European patent application No. 80300505.7, published Sept. 17, 1980 (Pub. No. 15,683), European patent application No. 81303837.9, published Mar. 3, 1982 (Pub. No. 46,677); European patent application No. 82306492.8, published Jul. 27, 1983 (Pub. No. 84,224); and European patent application No. 82303611.6, published Mar. 9, 1983 (Pub. No. 73,562), for description of methods for preparing heterocyclic amine derivatives.

A third method by which certain compounds of Formula IV may be obtained is shown in Equation 5.

Equation 5

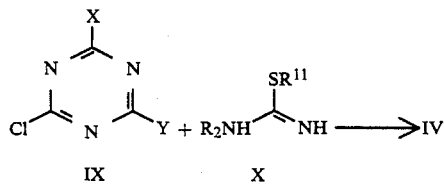

wherein
R, R'', X and Y are as previously defined.

The reaction of Equation 5 may be carried out by contacting a chlorotriazine of Formula IX with an S-alkyl isothiourea of Formula X in the same manner as was described in the reaction of Equation 2.

Compounds of Formulae Ib and Ic may be obtained from those of Formula Ia by the reactions of Equation 6.

Equation 6

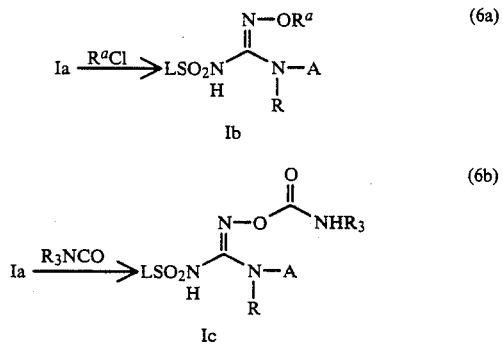

wherein
$R^a$ is $C(O)R_1$, $C(O)NR_2R_3$, or $CO_2R_4$, and L, R, $R_1$, $R_2$, $R_3$, $R_4$, and A are as previously defined.

The reaction of Equation 6a is carried out by contacting Ia with 1–10 equivalents of the appropriate carboxylic acid chloride or anhydride, or alkyl chloroformate, or dialkyl carbamoyl chloride in the presence of an acid scavenger, such as pyridine or a tertiary amine, at 0° to 40° for 2 to 24 hours, adding ice-water, and filtering or extracting the product into an organic solvent.

The reaction of Equation 6b may be conducted by treating a solution of Ia in an inert solvent such as methylene chloride or acetonitrile with 1–1.5 equivalents of an alkyl isocyanate at 20°–80° for 1 to 24 hours. The product is isolated by concentrating the reaction mixture and trituration with a solvent such as ether or chlorobutane.

Additional methods for preparation of compounds of this invention are described in South African patent application 84/4808.

Agriculturally suitable salts of compounds of Formulae I and II are also useful herbicides. Salts of compounds of Formulae I and II can be prepared in a number of ways known to the art. For example, metal salts can be made by treating compounds of Formulae I and II with a solution of an alkali or alkaline earth metal salt having a sufficiently basic anion (e.g., hydroxide, alkoxide, carbonate or hydride). Quaternary amine salts can be made by similar techniques.

Salts of compounds of Formulae I and II can also be prepared by exchange of one cation for another. Cationic exchange can be effected by direct treatment of an aqueous solution of a salt of a compound of Formulae I and II (e.g., alkali metal or quaternary amine salt) with a solution containing the cation to be exchanged. This method is most effective when the desired salt containing the exchanged cation is insoluble in water, e.g., a copper salt, and can be separated by filtration.

Exchange may also be effected by passing an aqueous solution of a salt of a compound of Formulae I and II (e.g., an alkali metal or quaternary amine salt) through a column packed with a cation exchange resin containing the cation to be exchanged. In this method, the cation of the resin is exchanged for that of the original salt and the desired product is eluted from the column. This method is particularly useful when the desired salt is water-soluble, e.g., a potassium, sodium or calcium salt.

Acid addition salts, useful in this invention, can be obtained by reacting a compound of Formulae I and II with a suitable acid, e.g., p-toluenesulfonic acid, trichloroacetic acid or the like. The disclosures of all references cited above are herein incorporated by reference.

In the following examples, all parts are by weight and temperatures in °C. unless otherwise indicated.

EXAMPLE 1

2-Chloro-N-[[(4,6-dimethylpyrimidin-2-yl)amino]hydroxyiminomethyl]benzenesulfonamide To a solution of 0.5 g of methyl N'-(2-chlorophenylsulfonyl)-N-(4,6-dimethylpyrimdin-2-yl)carbamimidothioate in 10 ml of tetrahydrofuran was added 0.3 g of hydroxylamine hydrochloride and 0.3 g of sodium acetate. The mixture was stirred at room temperature for 2 hours, whereupon the product was precipitated with ice-water, filtered, washed with water, and dried by suction to afford 0.3 g of the title compound, m.p. 165°–167°. NMR(CDCl$_3$/DMSO-d$_6$) δ2.6 (s, 6), 6.8 (s, 1), 7.4 (m, 3), 8.2 (m, 1), 10.2 (br, 1), 12.0 (br, 1). m/e: 355 (M+).

EXAMPLE 2

N-(4,6-Dimethylpyrimidin-2-yl)thiourea

A suspension of 10 g of 2-cyanoamino-4,6-dimethylpyrimidine in 50 ml of pyridine was saturated with hydrogen sulfide and stored for 1 hour at 25°. The H$_2$S treatment was repeated twice more, and the mixture was allowed to stir at 25° for 16 hours. Methylene chloride was added, and the product was filtered and washed with methylene chloride to afford 8 g of 4,6-dimethylpyrimidin-2-yl thiourea, m.p. >260°. IR (Nujol) 3280, 3180, 3120, 1610 cm$^{-1}$.

EXAMPLE 3

N-[(4-Methoxy-6-methylpyrimidin-2-yl)aminothioxomethyl]benzamide

To a hot solution of 14 g of ammonium thiocyanate in 300 ml of acetonitrile was added 24 ml of benzoyl chloride. The mixture was heated on the steam bath for 30 minutes and filtered. The filtrate was heated with 21 g of 4-methoxy-6-methylpyrimidine-2-amine for 30 minutes and cooled. The product was collected by filtration and washed with a little acetonitrile to provide 28 g of N-[[(4-methoxy-6-methylpyrimidin-2-yl)aminothiocarbonyl]amino]benzamide, m.p. 193°–195°. IR (Nujol) 3290, 1720 cm$^{-1}$.

EXAMPLE 4

N-(4-Methoxy-6-methylpyrimidin-2-yl)thiourea

A mixture of 25 g of the compound from Example 3 and 55 ml of 10% aqueous sodium hydroxide was heated on the steam bath for 30 minutes, cooled, neutralized with aqueous HCl to pH 8, filtered, washed with water, dried by suction, and washed with ether to afford 16 g of the title compound, m.p. 220° d.

Anal. Calc'd.: C: 42.4, H: 5.06, N: 28.2, S: 16.2 Found: C: 42.6, H: 4.8, N: 28.8, S: 15.3 m/e 198 (M+).

EXAMPLE 5

Methyl 2-[[1-(4-methoxy-6-methylpyrimidin-2-ylimino)-1-(methylthio)methyl]aminosulfonyl]benzoate To 9 g of the compound from Example 4 and 100 ml of tetrahydrofuran was added 7.6 g of dimethyl sulfate and the mixture was stirred for 2 days at room temperature. The product was filtered and washed with a little tetrahydrofuran to give 22 g of crude product. Five grams of this material was suspended in 150 ml of methylene chloride and 1 ml of water, and 5 g of sodium bicarbonate and 6 g of methyl 2-chlorosulfonyl benzoate were added. The mixture was stirred for 24 hours, washed with dilute aqueous HCl, dried with sodium sulfate, filtered, and chromatographed on silica gel to afford 2.8 g of the title compound as a crystalline solid, m.p. 143°–144°.

Anal. Calc'd.: C: 45.22, H: 4.55, N: 14.06, S: 16.1 Found: C: 46.8, H: 4.35, N: 13.2, S: 16 m/e 395 (M+—CH$_3$), NMR(CDCl$_3$) δ2.35 (s, 3), 2.45 (s, 3), 3.90 (s, 3), 4.0 (s, 3) 6.35 (s, 1), 7.7 (m, 3), 8.2 (m, 1), 10.8 (brs. 1).

EXAMPLE 6

Methyl N-(4,6-dimethoxy-1,3,5-triazin-2-yl)carbaminidothioate

A mixture of 20 g of 2-chloro-4,6-dimethoxy-s-triazine, 20 g of S-methyl isothiouronium sulfate, 16 g of sodium carbonate, and 50 ml of water was stirred for 72 hours, concentrated at reduced pressure, and extracted with 300 ml of methylene chloride. The organic layer was dried with Na$_2$SO$_4$, filtered, concentrated to dryness, and recrystallized from chlorobutane to afford 10 g of title compound, m.p. 94°–100°. NMR(CDCl$_3$) δ2.6 (s, 3), 4.0 (s, 6), 8.2 (brs, 1).

Using the procedures and examples shown above, the compounds in Tables 1-13 can be prepared.

TABLE 1a

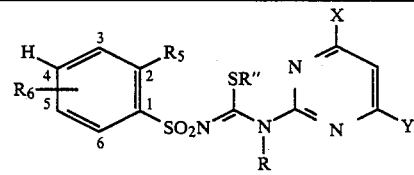

| R$_5$ | R$_6$ | R''' | R | X | Y | m.p. (°C.) |
|---|---|---|---|---|---|---|
| SCH$_2$CH=CH$_2$ | 3-Cl | CH$_3$ | H | OCH$_3$ | OCH$_3$ | |
| SCH$_2$CH=CH$_2$ | H | C$_2$H$_5$ | H | OCH$_3$ | OC$_2$H$_5$ | |
| OSO$_2$—n-C$_3$H$_7$ | H | CH$_3$ | CH$_3$ | CH$_3$ | CH$_2$OCH$_3$ | |
| OSO$_2$—n-C$_3$H$_7$ | H | CH$_3$ | H | CH$_3$ | SCH$_3$ | |
| OSO$_2$CH$_3$ | H | CH$_3$ | H | OCH$_3$ | CH$_3$ | |
| OSO$_2$CH$_3$ | H | CH$_3$ | H | OCH$_3$ | OCH$_3$ | |
| CH$_2$CH$_3$ | 5-Br | CH$_3$ | H | CH$_3$ | OCH$_3$ | |
| CH$_2$CH$_3$ | H | CH$_3$ | H | CH$_3$ | CH$_3$ | |
| n-C$_4$H$_9$ | H | n-C$_3$H$_7$ | H | OCH$_3$ | OCH$_3$ | |
| i-C$_3$H$_7$ | H | CH$_3$ | CH$_3$ | OCH$_3$ | CH$_3$ | |
| OSO$_2$N(CH$_3$)$_2$ | H | CH$_3$ | H | CH$_3$ | CH(OCH$_2$CH$_2$O) | |
| OCH$_2$CH$_3$ | H | CH$_3$ | H | CH$_3$ | CH$_3$ | |
| OCH$_2$CH$_3$ | H | CH$_3$ | H | CH$_3$ | OCH$_3$ | |
| O—i-C$_3$H$_7$ | H | CH$_3$ | H | OCH$_3$ | OCH$_3$ | |
| O—i-C$_3$H$_7$ | H | CH$_3$ | H | OCH$_3$ | C$_2$H$_5$ | |
| O—n-C$_4$H$_9$ | H | CH$_3$ | H | CH$_3$ | CH(OCH$_3$)$_2$ | |
| O—n-C$_4$H$_9$ | H | CH$_3$ | H | CH$_3$ | OC$_2$H$_5$ | |
| SO$_2$CF$_2$H | 5-CH$_3$ | CH$_3$ | H | OCH$_3$ | OCH$_3$ | |
| SO$_2$CF$_2$H | H | C$_2$H$_5$ | H | OCH$_3$ | OC$_2$H$_5$ | |
| SCF$_2$H | 6-SCH$_3$ | CH$_3$ | CH$_3$ | CH$_3$ | CH$_2$OCH$_3$ | |
| SCF$_2$H | H | CH$_3$ | H | CH$_3$ | SCH$_3$ | |
| OCF$_3$ | H | CH$_3$ | H | OCH$_3$ | CH$_3$ | |
| OCF$_3$ | H | CH$_3$ | H | OCH$_3$ | OCH$_3$ | |
| CH$_2$OCH$_3$ | H | n-C$_3$H$_7$ | H | OCH$_3$ | OCH$_3$ | |
| CH$_2$OCH$_3$ | H | CH$_3$ | CH$_3$ | OCH$_3$ | CH$_3$ | |
| CH$_2$OCH$_2$CH$_3$ | H | CH$_3$ | H | Cl | OCH$_3$ | |

TABLE 1a-continued

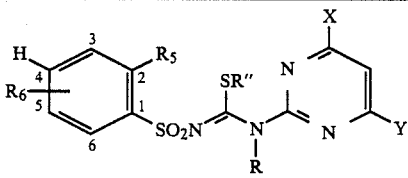

| R5 | R6 | R″ | R | X | Y | m.p. (°C.) |
|---|---|---|---|---|---|---|
| CH2OCH2CH3 | H | CH3 | H | Cl | CH3 | |
| OCF2H | H | CH3 | H | OCH3 | CH3 | |
| OCF2H | H | CH3 | H | CH3 | CH(OCH2CH2O) | |

TABLE 1b

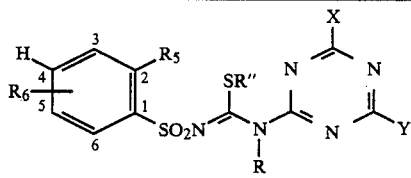

| R5 | R6 | R″ | R | X | Y | m.p. (°C.) |
|---|---|---|---|---|---|---|
| SO2CH2CH=CH2 | H | CH3 | H | OCH3 | OCH3 | |
| SO2CH2CH=CH2 | H | CH3 | H | OCH3 | C2H5 | |
| OSO2—n-C3H7 | H | CH3 | CH3 | CH3 | CH2OCH3 | |
| OSO2—n-C3H7 | H | CH3 | H | CH3 | SCH3 | |
| OSO2CH3 | H | CH3 | H | OCH3 | CH3 | |
| OSO2CH3 | H | CH3 | H | OCH3 | OCH3 | |
| CH2CH3 | 3-Br | CH3 | H | CH3 | OCH3 | |
| CH2CH3 | H | CH3 | H | CH3 | CH3 | |
| n-C4H9 | H | n-C3H7 | H | OCH3 | OCH3 | |
| i-C3H7 | H | CH3 | CH3 | OCH3 | CH3 | |
| OSO2N(CH3)2 | H | CH3 | H | CH3 | CH(OCH2CH2O) | |
| OCH2CH3 | H | CH3 | H | CH3 | CH3 | |
| OCH2CH3 | H | CH3 | H | CH3 | OCH3 | |
| O—i-C3H7 | H | CH3 | H | OCH3 | OCH3 | |
| O—i-C3H7 | H | CH3 | H | OCH3 | C2H5 | |
| O—n-C4H9 | H | CH3 | H | CH3 | CH(OCH3)2 | |
| O—n-C4H9 | H | CH3 | H | CH3 | OC2H5 | |
| SO2CF2H | 6-SCH3 | CH3 | H | OCH3 | OCH3 | |
| SO2CF2H | H | C2H5 | H | OCH3 | OC2H5 | |
| SCF2H | H | CH3 | CH3 | CH3 | CH2OCH3 | |
| SCF2H | H | CH3 | H | CH3 | SCH3 | |
| OCF3 | H | CH3 | H | OCH3 | CH3 | |
| OCF3 | H | CH3 | H | OCH3 | OCH3 | |
| CH2OCH3 | H | n-C3H7 | H | OCH3 | OCH3 | |
| CH2OCH3 | H | CH3 | CH3 | OCH3 | CH3 | |
| CH2OCH2CH3 | H | CH3 | H | Cl | OCH3 | |
| CH2OCH2CH3 | H | CH3 | H | Cl | CH3 | |
| OCF2H | H | CH3 | H | OCH3 | CH3 | |
| OCF2H | H | CH3 | H | OCH3 | OCH3 | |
| OCF2H | H | CH3 | H | CH3 | CH3 | |
| CH2CH2OC2H5 | H | CH3 | H | OCH3 | CH3 | |

TABLE 1c

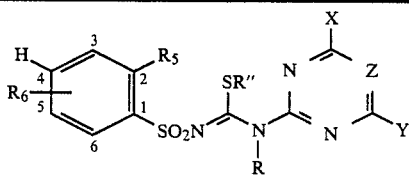

| R″ | R | R5 | R6 | X | Y | Z | m.p. (°C.) |
|---|---|---|---|---|---|---|---|
| CH3 | H | OCH2CH2OCH3 | H | CH3 | H | CH | |
| CH3 | H | OCH2CH=CH2 | H | CH3 | CH3 | N | |
| CH3 | H | OCH2CH≡CH | 6-OCH3 | CH3 | CH3 | CH | |
| CH3 | H | C6H5 | H | CH3 | CH3 | N | |

TABLE 1c-continued

| R" | R | R$_5$ | R$_6$ | X | Y | Z | m.p. (°C.) |
|---|---|---|---|---|---|---|---|
| CH$_3$ | H | (3,5-dimethylisoxazol-4-yl: N—N / \\ CH$_3$, CH$_3$, O) | H | CH$_3$ | OCH$_3$ | CH | |
| CH$_3$ | H | (3-methyl-1,2,4-oxadiazol-5-yl) | H | OCH$_3$ | OCH$_3$ | N | |
| CH$_3$ | H | (2-thienyl) | H | OCH$_3$ | OCH$_2$C≡CH | N | |
| CH$_3$ | H | (2-furyl) | H | OCH$_3$ | OCH$_2$CH$_2$OCH$_3$ | N | |
| CH$_3$ | H | C$_2$H$_5$ | H | OCH$_3$ | OCF$_2$H | CH | |
| CH$_3$ | H | OCF$_3$ | H | OCH$_3$ | SCF$_2$H | CH | |
| CH$_3$ | H | SO$_2$CH$_3$ | 3-OCF$_2$H | OCH$_3$ | C(CH$_3$)(OCH$_3$)$_2$ | CH | |
| CH$_3$ | H | OCH$_2$CH$_3$ | H | OCH$_3$ | CF$_3$ | N | |
| CH$_3$ | H | SO$_2$CH$_2$CH$_3$ | H | OCH$_3$ | N(CH$_3$)$_2$ | CH | |
| CH$_3$ | CH$_3$ | SO$_2$CH$_2$CH$_3$ | H | OCH$_3$ | C(CH$_3$)(SCH$_3$)$_2$ | N | |
| CH$_3$ | H | SO$_2$CH$_2$CH$_3$ | H | OCF$_2$H | CH(SCH$_2$CH$_2$S) | CH | |
| CH$_3$ | H | SO$_2$CH$_2$CH$_3$ | H | CF$_3$ | CH$_2$CH$_3$ | CH | |
| CH$_3$ | H | SO$_2$CH$_2$CH$_3$ | H | F | OCH$_3$ | CH | |
| CH$_3$ | H | SO$_2$CH$_2$CH$_3$ | H | OC$_2$H$_5$ | C(CH$_3$)(OCH$_2$CH$_2$O) | CH | |

TABLE 1d

| R" | R | L | X | Y | Z | m.p. (°C.) |
|---|---|---|---|---|---|---|
| CH$_3$ | H | L$_2$:R$_7$ = Cl | CH$_3$ | H | CH | |
| CH$_3$ | H | L$_2$:R$_7$ = OCH$_3$ | CH$_3$ | CH$_3$ | CH | |
| CH$_3$ | H | L$_2$:R$_7$ = SO$_2$N(CH$_3$)$_2$ | CH$_3$ | CH$_3$ | CH | |
| CH$_3$ | H | L$_3$:R$_8$ = SO$_2$N(CH$_3$)$_2$ | CH$_3$ | CH$_3$ | CH | |
| CH$_3$ | H | L$_3$:R$_8$ = SO$_2$CH$_3$ | CH$_3$ | OCH$_3$ | CH | |
| CH$_3$ | CH$_3$ | L$_3$:R$_8$ = SO$_2$CH$_2$CH$_3$ | Cl | OCH$_3$ | CH | |
| i-C$_3$H$_7$ | H | L$_4$:R$_9$ = Br | OCH$_3$ | OCH$_3$ | CH | |
| CH$_3$ | H | L$_5$:R$_9$ = C$_2$H$_5$ | OCH$_3$ | OCH$_2$CH=CH$_2$ | CH | |
| CH$_3$ | H | L$_6$:R$_9$ = Cl | OCH$_3$ | OCH$_2$C≡CH | N | |
| CH$_3$ | H | L$_7$:R$_{10}$ = CO$_2$CH$_3$ | OCH$_3$ | OCH$_2$CF$_3$ | N | |
| CH$_3$ | H | L$_8$:Q$_1$ = O, m = 0, R$_{11}$ = R$_{12}$ = R$_{13}$ = CH$_3$ | OCH$_3$ | CH$_2$SCH$_3$ | CH | |
| CH$_3$ | H | L$_9$:Q$_2$ = S, R$_{14}$ = R$_{15}$ = H | OCH$_3$ | OCF$_2$H | CH | |
| CH$_3$ | H | L$_{10}$:m = 0, R$_{13}$ = H, R$_{16}$ = CH$_3$ | OCH$_3$ | SCF$_2$H | CH | |
| CH$_3$ | H | L$_{11}$:m = 0, R$_{13}$ = H | OCH$_3$ | C(CH$_3$)(OCH$_3$)$_2$ | CH | |
| CH$_3$ | H | L$_{12}$:m = 1, R$_{13}$ = CH$_3$ | OCH$_3$ | CF$_3$ | CH | |
| CH$_3$ | H | L$_{13}$:m = 0, R$_{13}$ = H | OCH$_3$ | N(CH$_3$)$_2$ | CH | |
| CH$_3$ | CH$_3$ | L$_{14}$:R$_{16}$ = CH$_2$CH$_3$ | OCH$_3$ | C(CH$_3$)(SCH$_3$)$_2$ | CH | |
| CH$_3$ | H | L$_{15}$:R$_{17}$ = CH$_3$ | OCF$_2$H | CH(SCH$_2$CH$_2$S) | CH | |
| CH$_3$ | H | L$_{16}$:R$_{17}$ = H | CF$_3$ | CH$_2$CH$_3$ | CH | |
| CH$_3$ | H | L$_{17}$:R$_{17}$ = R$_{18}$ = CH$_3$ | F | OCH$_3$ | CH | |
| CH$_3$ | H | L$_{17}$:R$_{17}$ = R$_{18}$ = CH$_3$ | OC$_2$H$_5$ | C(CH$_3$)(OCH$_2$CH$_2$O) | CH | |

TABLE 1e

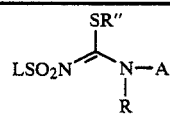

| L | R″ | R | A | m.p. (°C.) |
|---|---|---|---|---|
| $L_1$:$R_5$ = $CO_2CH_3$, $R_6$ = H | $CH_3$ | H | $A_4$:$X_1$ = $CH_3$, $Y_2$ = H | |
| $L_1$:$R_5$ = $SO_2CH_3$, $R_6$ = H | $CH_3$ | H | $A_5$:$X_2$ = $CH_2CH_3$, $Y_3$ = $SCH_3$ | |
| $L_1$:$R_5$ = $NO_2$, $R_6$ = H | $CH_3$ | H | $A_6$:$X_3$ = $OCH_3$ | |
| $L_1$:$R_5$ = Br, $R_6$ = H | $CH_3$ | H | $A_3$:$X_1$ = $OCH_3$ | |
| $L_1$:$R_5$ = Cl, $R_6$ = H | $CH_3$ | H | $A_5$:$X_2$ = $CH_3$, $Y_3$ = $OC_2H_5$ | |
| $L_1$:$R_5$ = $C_2H_5$, $R_6$ = H | $CH_3$ | H | $A_2$:$X_1$ = $OCH_3$, $Y_1$ = O | |
| $L_1$:$R_5$ = $SCF_3$, $R_6$ = H | $C_2H_5$ | H | $A_3$:$X_1$ = $OCF_2H$ | |
| $L_{17}$:$R_{17}$ = H, $R_{18}$ = $CH_3$ | $CH_3$ | H | $A_2$:$X_1$ = $OCH_3$, $Y_1$ = $CH_2$ | |
| $L_{16}$:$R_{17}$ = $CH_3$ | $CH_3$ | H | $A_3$:$X_1$ = $OCF_2H$ | |
| $L_2$:$R_7$ = $SCH_3$ | $CH_3$ | H | $A_4$:$X_1$ = $CH_3$, $Y_2$ = $CH_3$ | |
| $L_3$:$R_8$ = F | $CH_3$ | H | $A_5$:$X_2$ = $CH_2CH_3$, $Y_3$ = $OCH_3$ | |
| $L_4$:$R_9$ = i-$C_3H_7$ | $CH_3$ | H | $A_5$:$X_2$ = $CH_3$, $Y_3$ = $CH_2CH_3$ | |
| $L_5$:$R_9$ = $SO_2CH_3$ | $CH_3$ | H | $A_6$:$X_3$ = $OCH_3$ | |
| $L_6$:$R_9$ = $SO_2CH_3$ | $CH_3$ | H | $A_2$:$X_1$ = $OCH_3$, $Y_1$ = O | |
| $L_7$:$R_{10}$ = $OCH_2CH_3$ | $CH_3$ | H | $A_3$:$X_1$ = $CH_3$ | |
| $L_8$:$Q_1$ = S, $R_{11}$ = $R_{12}$ = $CH_3$, m = 1, $R_{13}$ = H | $CH_3$ | H | $A_6$:$X_3$ = $CH_3$ | |
| $L_9$:$Q_2$ = O, $R_{14}$ = $R_{15}$ = $CH_3$ | $CH_3$ | H | $A_4$:$X_1$ = $OCH_3$, $Y_2$ = $CH_3$ | |
| $L_{10}$:$R_{16}$ = $C_2H_5$, $R_{13}$ = $CH_3$, m = 0 | $CH_3$ | H | $A_5$:$X_2$ = $CH_3$, $Y_3$ = $SCH_3$ | |
| $L_{11}$:m = 1, $R_{13}$ = H | $CH_3$ | H | $A_2$:$X_1$ = $CH_3$, $Y_1$ = $CH_2$ | |
| $L_{12}$:m = 0, $R_{13}$ = $CH_3$ | $CH_3$ | H | $A_2$:$X_1$ = $OCH_3$, $Y_1$ = $CH_2$ | |
| $L_{13}$:m = 1, $R_{13}$ = H | $CH_3$ | H | $A_5$:$X_2$ = $CH_2CF_3$, $Y_3$ = $CH_2CH_3$ | |
| $L_{14}$:$R_{16}$ = $CH_3$ | $CH_3$ | H | $A_4$:$X_1$ = $OCH_3$, $Y_2$ = H | |
| $L_{15}$:$R_{17}$ = $CH_3$ | $CH_3$ | H | $A_4$:$X_1$ = $OCH_3$, $Y_2$ = H | |

TABLE 2A

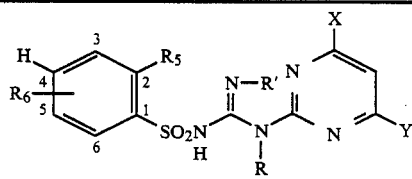

| $R_5$ | $R_6$ | R | R' | X | Y | m.p. (°C.) |
|---|---|---|---|---|---|---|
| Cl | H | H | OH | $CH_3$ | $CH_3$ | 165-167° |
| Cl | H | H | OH | $CH_3$ | $OCH_3$ | 121-128° |
| Cl | H | H | OH | $OCH_3$ | $OC_2H_5$ | |
| Cl | H | H | OH | $OCH_3$ | $OCH_3$ | 142-144° |
| F | H | H | OH | $CH_3$ | $CH_3$ | |
| F | H | H | OH | $CH_3$ | $OCH_3$ | |
| Br | H | H | OH | $OCH_3$ | $CH_3$ | |
| Br | H | H | OH | $OCH_3$ | $OCH_3$ | |
| $NO_2$ | H | H | OH | $CH_3$ | $CH(OCH_2CH_2O)$ | |
| $NO_2$ | H | $CH_3$ | OH | $CH_3$ | $C_2H_5$ | |
| $CF_3$ | H | H | OH | $OCH_3$ | $OC_2H_5$ | |
| $CF_3$ | H | H | OH | $OCH_3$ | $CH_3$ | |
| $OCH_3$ | H | H | OH | $CH_3$ | $OCH_3$ | |
| $OCH_3$ | H | H | OH | $CH_3$ | $CH(OCH_3)_2$ | |
| $OCH_3$ | H | H | OH | Cl | $CH_3$ | |
| $OCH_3$ | H | H | OH | Cl | $OCH_3$ | |
| $OC_2H_5$ | H | H | OH | $CH_3$ | $CH_2OCH_3$ | |
| $OC_2H_5$ | H | H | OH | $CH_3$ | $CH_3$ | |
| $OC_2H_5$ | H | $CH_3$ | OH | $OCH_3$ | $OCH_3$ | |
| O—i-$C_3H_7$ | H | H | OH | $OCH_3$ | $CH_3$ | |
| O—n-$C_3H_7$ | H | H | OH | $CH_3$ | $OCH_3$ | |
| O—n-$C_3H_7$ | H | H | OH | $CH_3$ | $CH_3$ | |
| O—i-$C_4H_9$ | H | H | OH | $OCH_3$ | $OCH_3$ | |
| O—i-$C_4H_9$ | H | H | OH | $OCH_3$ | $CH_3$ | |
| $CO_2CH_3$ | H | H | OH | $CH_3$ | $CH_3$ | $M^+$ = 379* |
| $CO_2CH_3$ | H | H | OH | $CH_3$ | $OCH_3$ | $M^+$ = 395* |
| $CO_2CH_3$ | H | H | OH | $OCH_3$ | $OC_2H_5$ | |
| $SO_2N(CH_3)_2$ | H | H | OH | $OCH_3$ | $OCH_3$ | |
| $SO_2N(CH_3)_2$ | H | H | OH | $CH_3$ | $CH_3$ | |
| $SO_2N(CH_3)_2$ | H | H | OH | $CH_3$ | $OCH_3$ | 166-168° |
| $SO_2N(CH_3)_2$ | H | H | OH | $OCH_3$ | $OCH_2CH_3$ | |
| $SO_2N(CH_3)_2$ | H | H | OH | $CH_3$ | $CH(OCH_2CH_2O)$ | |
| $SO_2N(CH_2CH_3)_2$ | H | $CH_3$ | OH | $CH_3$ | $C_2H_5$ | |
| $SO_2N(CH_2CH_3)_2$ | H | H | OH | $OCH_3$ | $OC_2H_5$ | |
| $SO_2N(CH_2CH_3)_2$ | H | H | OH | $OCH_3$ | $CH_3$ | |
| $CO_2CH_2CH_3$ | H | H | OH | $CH_3$ | $OCH_3$ | |

TABLE 2A-continued

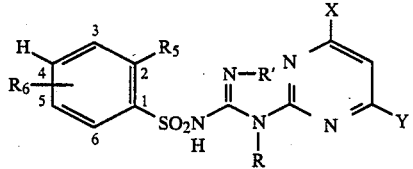

| R5 | R6 | R | R' | X | Y | m.p. (°C.) |
|---|---|---|---|---|---|---|
| CO2CH2CH3 | H | H | OH | CH3 | CH(OCH3)2 | |
| CO2CH3 | H | H | OH | Cl | CH3 | |
| CO2CH3 | H | H | OH | Cl | OCH3 | |
| CO2CH3 | H | H | OH | CH3 | CH2OCH3 | |
| CO2—i-C3H7 | H | H | OH | CH3 | CH3 | |
| CO2—i-C3H7 | H | CH3 | OH | OCH3 | OCH3 | |
| SO2N(OCH3)CH3 | H | H | OH | OCH3 | CH3 | |
| CO2CH2CH2OCH3 | H | H | OH | CH3 | OCH3 | |
| CO2CH2CH=CH2 | H | H | OH | CH3 | CH3 | |
| CO2CH2CH2Cl | H | H | OH | OCH3 | OCH3 | |
| CO2—n-C4H9 | H | H | OH | OCH3 | CH3 | |
| SO2CH3 | H | H | OH | CH3 | CH3 | |
| SO2CH3 | H | H | OH | CH3 | OCH3 | |
| SO2CH3 | H | H | OH | OCH3 | OC2H5 | |
| SO2CH3 | H | H | OH | OCH3 | OCH3 | |
| SO2CH2CH=CH2 | H | H | OH | CH3 | CH3 | |
| SO2CH2CH=CH2 | H | H | OH | CH3 | OCH3 | |
| SO2CH2CH2CH3 | H | H | OH | OCH3 | CH3 | |
| SCH2CH3 | H | H | OH | OCH3 | OCH3 | |
| SCF3 | H | H | OH | CH3 | CH(OCH2CH2O) | |
| SO2CHF2 | H | CH3 | OH | CH3 | C2H5 | |
| CH3 | H | H | OH | OCH3 | OC2H5 | |
| i-C3H7 | H | H | OH | OCH3 | CH3 | |
| n-C4H9 | H | H | OH | CH3 | OCH3 | |
| OSO2N(CH3)2 | H | H | OH | CH3 | CH(OCH3)2 | |
| OSO2N(CH3)2 | H | H | OH | Cl | CH3 | |
| OSO2CH(CH3)2 | H | H | OH | Cl | OCH3 | |
| OSO2C2H5 | H | H | OH | CH3 | CH2OCH3 | |
| OSO2CH3 | H | CH3 | OH | OCH3 | OCH3 | |
| OSO2CH3 | H | H | OH | OCH3 | CH3 | |
| CH2OCH3 | H | H | OH | OCH3 | OCH3 | |
| CH2CH2OCH3 | H | H | OH | CH3 | CH3 | |
| OCF3 | H | H | OH | OCH3 | OCH3 | |
| SO2—i-C3H7 | H | H | OH | OCH3 | CH3 | |
| Cl | H | H | CH3CO2 | CH3 | CH3 | 131–136° d |
| Cl | 5-CF3 | H | OH | CH3 | OCH3 | |
| Cl | H | H | CH3OCO2 | OCH3 | OC2H5 | |
| Cl | 6-SCH3 | H | OH | OCH3 | OCH3 | |
| F | 5-SCH3 | H | CH3CO2 | CH3 | CH3 | |
| F | 6-OCH3 | H | OH | CH3 | OCH3 | |
| Br | H | H | (CH3)2NCO2 | OCH3 | CH3 | |
| Br | 3-OCH3 | H | OH | OCH3 | OCH3 | |
| NO2 | H | H | CH3NHCO2 | CH3 | CH(OCH2CH2O) | |
| NO2 | 6-CH3 | CH3 | OH | CH3 | C2H5 | |
| CF3 | 5-CH3 | H | CF3CO2 | OCH3 | OC2H5 | |
| CF3 | 6-Cl | H | C2H5CO2 | OCH3 | CH3 | |
| OCH3 | H | H | C2H5OCO2 | CH3 | OCH3 | |
| OCH3 | 5-Cl | H | OH | CH3 | CH(OCH3)2 | |
| OCH3 | 3-Cl | H | OH | Cl | CH3 | |
| OCH3 | H | H | CH3CO2 | Cl | OCH3 | |
| OC2H5 | 5-F | H | OH | CH3 | CH2OCH3 | |
| OC2H5 | 5-F | H | Et2NCO2 | CH3 | CH3 | |
| OC2H5 | 3-Br | CH3 | OH | OCH3 | OCH3 | |
| O—i-C3H7 | H | H | EtOCO2 | OCH3 | CH3 | |
| O—n-C3H7 | H | H | O—n-C3H7 | CH3 | OCH3 | |
| O—n-C3H7 | 6-CH3 | H | OH | CH3 | CH3 | |
| O—i-C4H9 | 3-CF3 | H | CH3OCO2 | OCH3 | OCH3 | |
| O—i-C4H9 | 6-CF3 | H | OH | OCH3 | CH3 | |
| CO2CH3 | 5-CF3 | H | OH | CH3 | CH3 | |
| CO2CH3 | 6-CF3 | H | OH | CH3 | OCH3 | |
| CO2CH3 | H | H | OH | CH3OCO2CH3 | OC2H5 | |
| SO2N(CH3)3 | 6-SCH3 | H | OH | OCH3 | OCH3 | |
| SO2N(CH3)3 | 5-SCH3 | H | CH3CO2 | CH3 | CH3 | |
| SO2N(CH3)3 | 6-OCH3 | H | OH | CH3 | OCH3 | |
| SO2N(CH3)3 | H | H | (CH3)2NCO2 | OCH3 | OCH3 | |
| SO2N(CH3)3 | 3-OCH3 | H | OH | OCH3 | OCH2CH3 | |
| SO2N(CH3)3 | H | H | CH3NHCO2 | CH3 | CH(OCH2CH2O) | |
| SO2N(CH2CH3)3 | 3-CH3 | CH3 | OH | CH3 | C2H5 | |
| SO2N(CH2CH3)3 | 5-CH3 | H | CF3CO2 | OCH3 | OC3H5 | |
| SO2N(CH2CH3)3 | 6-Cl | H | C2H5CO2 | OCH3 | CH3 | |
| CO2CH2CH3 | H | H | C2H5CO2 | CH3 | OCH3 | |
| CO2CH2CH3 | H | H | C2H5CO2 | CH3 | OCH3 | |

TABLE 2A-continued

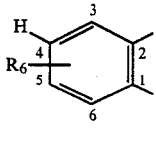

| R5 | R6 | R | R' | X | Y | m.p. (°C.) |
|---|---|---|---|---|---|---|
| CO2CH3 | H | H | CH3OCO2 | Cl | OCH3 | |
| CO2CH3 | 5-F | H | OH | CH3 | CH2OCH3 | |
| CO2—i-C3H7 | 5-F | H | (C2H5)2NCO2 | CH3 | CH3 | |
| CO2—i-C3H7 | 3-Br | CH3 | OH | OCH3 | OCH3 | |
| SO2N(OCH3)CH3 | H | H | n-C3H7CO2 | OCH3 | CH3 | |
| CO2CH2CH2OCH3 | H | H | OH | CH3 | CH3 | |
| CO2CH2CH=CH2 | 6-CH3 | H | OH | CH3 | CH3 | |
| CO2CH2CH2Cl | 3-CF3 | h | OH | OCH3 | OCH3 | |
| CO2—n-C4H9 | 6-CF3 | H | OH | OCH3 | CH3 | |
| SO2CH3 | 5-CF3 | H | OH | CH3 | CH3 | |
| SO2CH3 | 3-CF3 | H | OH | CH3 | OCH3 | |
| SO2CH3 | H | H | CH3OCO2 | OCH3 | OC2H5 | |
| SO2CH3 | 6-SCH3 | H | OH | OCH3 | OCH3 | |
| SO2CH2CH=CH2 | 5-SCH3 | H | CH3CO2 | CH3 | CH3 | |
| SO2CH2CH=CH2 | 6-OCH3 | H | OH | CH3 | OCH3 | |
| SO2CH2CH2CH3 | H | H | (CH3)2NCO3 | OCH3 | CH3 | |
| SCH2CH3 | 3-OCH3 | H | OH | OCH3 | OCH3 | |
| SCF3 | H | H | CH3NHCO2 | CH3 | CH(OCH2CH2O) | |
| SO2CHF2 | 3-CH3 | CH3 | OH | CH3 | C2H5 | |
| CH3 | 5-CH3 | H | CF3CO2 | OCH3 | OC2H5 | |
| i-C3H7 | 6-Cl | H | OH | OCH3 | CH3 | |
| n-C4H9 | H | H | C2H5CO2 | CH3 | OCH3 | |
| OSO2N(CH3)2 | 6-Cl | H | OH | Cl | CH3 | |
| OSO2N(CH3)2 | H | H | CH3OCO2 | Cl | OCH3 | |
| OSO2CH(CH3)2 | 5-F | H | CH3CO2 | CH3 | CH2OCH3 | |
| OSO2CH3 | 3-Br | CH3 | OH | OCH3 | OCH3 | |
| OSO2CH3 | H | H | n-C3H7OCO2 | OCH3 | CH3 | |
| CH2OCH3 | H | H | C3H7CO2 | CH3 | OCH3 | |
| CH2CH2OCH3 | 6-CH3 | H | OH | CH3 | CH3 | |
| OCF3 | 3-CF3 | H | OH | OCH3 | OCH3 | |
| SO2—i-C3H7 | 5-CF3 | H | OH | OCH3 | CH3 | |
| CH2CH2OC2H5 | H | H | OH | OCH3 | OCH3 | |
| C6H5 | 6-Cl | H | OCH3 | OCH3 | OCH3 | |
| C6H5 | 6-Cl | H | OCH3 | OCH3 | CH3 | |
| C6H5 | 6-OCH3 | H | OCH3 | OCH3 | CH3 | |
| C6H5 | 6-OCH3 | H | OCH3 | OCH3 | OCH3 | |

*Data refer to molecular ion in electron-impact mass spectrum.

TABLE 2B

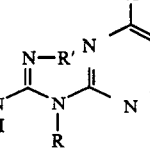

| R5 | R6 | R | R' | X | Y | m.p. (°C.) |
|---|---|---|---|---|---|---|
| Cl | H | H | OH | CH3 | CH3 | |
| Cl | H | H | OH | CH3 | OCH3 | |
| Cl | H | H | OH | OCH3 | OC2H5 | |
| Cl | H | H | OH | OCH3 | OCH3 | 137–140° |
| F | H | H | OH | CH3 | CH3 | |
| F | H | H | OH | CH3 | OCH3 | |
| Br | H | H | OH | OCH3 | CH3 | |
| Br | H | OH | OCH3 | OCH3 | | |
| NO2 | H | H | OH | CH3 | CH(OCH2CH2O) | |
| NO2 | H | CH3 | OH | CH3 | C2H5 | |
| CF3 | H | H | OH | OCH3 | OC2H5 | |
| CF3 | H | H | OH | OCH3 | CH3 | |
| OCH3 | H | H | OH | CH3 | OCH3 | |
| OCH3 | H | H | OH | CH3 | CH(OCH3) | |
| OCH3 | H | H | OH | CH3 | CH3 | |
| OCH3 | H | H | OH | OCH3 | OCH3 | |
| OC2H5 | H | H | OH | CH3 | CH2OCH3 | |
| OC2H5 | H | H | OH | CH3 | CH3 | |
| OC2H5 | H | CH3 | OH | OCH3 | OCH3 | |
| O—i-C3H7 | H | H | OH | OCH3 | CH3 | |

TABLE 2B-continued

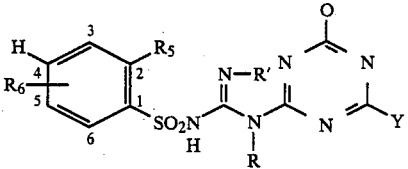

| R₅ | R₆ | R | R' | X | Y | m.p. (°C.) |
|---|---|---|---|---|---|---|
| O—i-C₃H₇ | H | H | OH | CH₃ | OCH₃ | |
| O—i-C₃H₇ | H | H | OH | CH₃ | CH₃ | |
| O—i-C₃H₇ | H | H | OH | OCH₃ | OCH₃ | |
| O—i-C₃H₇ | H | H | OH | OCH₃ | CH₃ | |
| CO₂CH₃ | H | H | OH | CH₃ | CH₃ | |
| CO₂CH₃ | H | H | OH | CH₃ | OCH₃ | |
| CO₂CH₃ | H | H | OH | OCH₃ | OC₂H₅ | |
| SO₂N(CH₃)₂ | H | H | OH | OCH₃ | OCH₃ | δ 3.0 and 4.0 (1:1)** |
| SO₂N(CH₃)₂ | H | H | OH | CH₃ | CH₃ | 4.O (1:1)* |
| SO₂N(CH₃)₂ | H | H | OH | H | OCH₃ | |
| SO₂N(CH₃)₂ | H | H | OH | OCH₃ | OCH₃ | |
| SO₂N(CH₃)₂ | H | H | OH | CH₃ | CH(OCH₂CH₂O) | |
| SO₂N(CH₃)₂ | H | CH₃ | OH | CH₃ | C₂H₅ | |
| SO₂N(CH₃)₂ | H | H | OH | OCH₃ | OC₂H₅ | |
| SO₂N(CH₃)₂ | H | H | OH | OCH₃ | CH₃ | |
| CO₂CH₂CH₃ | H | H | OH | CH₃ | OCH₃ | |
| CO₂CH₂CH₃ | H | H | OH | CH₃ | CH(OCH₃)₂ | |
| CO₂CH₃ | H | H | OH | CH₃ | CH₃ | |
| CO₂CH₃ | H | H | OH | CH₃ | OCH₃ | |
| CO₂CH₃ | H | H | OH | CH₃ | CH₂OCH₃ | |
| CO₂—i-C₃H₇ | H | H | OH | CH₃ | CH₃ | |
| CO₂—i-C₃H₇ | H | H | OH | OCH₃ | OCH₃ | |
| SO₂N(OCH₃)CH₃ | H | H | OH | OCH₃ | CH₃ | |
| CO₂CH₂CH₂OCH₃ | H | H | OH | OCH₃ | OCH₃ | |
| CO₂CH₂CH=CH₂ | H | H | OH | CH₃ | CH₃ | |
| CO₂CH₂CH₂Cl | H | H | OH | OCH₃ | OCH₃ | |
| CO₂—n-C₄H₉ | H | H | OH | OCH₃ | OCH₃ | |
| SO₂CH₃ | H | H | OH | CH₃ | CH₃ | |
| SO₂CH₃ | H | H | OH | CH₃ | OCH₃ | |
| SO₂CH₃ | H | H | OH | OCH₃ | OC₂H₅ | |
| SO₂CH₃ | H | H | OH | OCH₃ | OCH₃ | |
| SO₂CH₂CH=CH₂ | H | H | OH | CH₃ | CH₃ | |
| SO₂CH₂CH=CH₂ | H | H | OH | CH₃ | OCH₃ | |
| SO₂CH₂CH₂CH₃ | H | H | OH | OCH₃ | OCH₃ | |
| SCH₂CH₃ | H | H | OH | OCH₃ | OCH₃ | |
| SCF₃ | H | H | OH | CH₃ | CH(OCH₂CH₂O) | |
| SO₂CHF₂ | H | CH₃ | OH | CH₃ | C₂H₅ | |
| CH₃ | H | H | OH | OCH₃ | OC₂H₅ | |
| i-C₃H₇ | H | H | OH | OCH₃ | CH₃ | |
| n-C₄H₉ | H | H | OH | CH₃ | OCH₃ | |
| OSO₂N(CH₃)₂ | H | H | OH | CH₃ | CH(OCH₃)₂ | |
| OSO₂N(CH₃)₂ | H | H | OH | CH₃ | CH₃ | |
| OSO₂CH(CH₃)₂ | H | H | OH | CH₃ | OCH₃ | |
| OSO₂C₂H₅ | H | H | OH | CH₃ | CH₂OCH₃ | |
| OSO₂CH₃ | H | CH₃ | OH | OCH₃ | OCH₃ | |
| OSO₂CH₃ | H | H | OH | OCH₃ | CH₃ | |
| CH₂OCH₃ | H | H | OH | CH₃ | OCH₃ | |
| CH₂CH₂OCH₃ | H | H | OH | CH₃ | CH₃ | |
| OCF₃ | H | H | OH | OCH₃ | OCH₃ | |
| SO₂—i-C₃H₇ | H | H | OH | OCH₃ | CH₃ | |
| Cl | 3-CF₃ | H | OH | CH₃ | CH₃ | |
| Cl | 5-CF₃ | H | OH | CH₃ | OCH₃ | |
| Cl | H | H | CH₃OCO₂ | OCH₃ | OC₂H₅ | |
| Cl | 6-SCH₃ | H | OH | OCH₃ | OCH₃ | |
| F | 5-SCH₃ | H | CH₃CO₂ | CH₃ | CH₃ | |
| F | 6-OCH₃ | H | OH | CH₃ | OCH₃ | |
| Br | H | H | (CH₃)₂NCO₂ | OCH₃ | CH₃ | |
| Br | 3-OCH₃ | H | OH | OCH₃ | OCH₃ | |
| NO₂ | H | H | CH₃NHCO₂ | CH₃ | CH(OCH₂CH₂O) | |
| NO₂ | 3-CH₃ | CH₃ | OH | CH₃ | C₂H₅ | |
| CF₃ | 5-CH₃ | H | CF₃CO₂ | OCH₃ | OC₂H₅ | |
| CF₃ | 6-Cl | H | C₂H₅CO₂ | OCH₃ | CH₃ | |
| OCH₃ | H | H | C₂H₅OCO₂ | OCH₃ | OCH₃ | |
| OCH₃ | 5-Cl | H | OH | CH₃ | CH(OCH₃)₂ | |
| OCH₃ | 6-Cl | H | OH | CH₃ | CH₃ | |
| OCH₃ | H | H | n-C₃H₇CO₂ | CH₃ | OCH₃ | |
| OC₂H₅ | 5-F | H | OH | CH₃ | CH₂OCH₃ | |
| OC₂H₅ | 5-F | H | Et₂NCO₂ | CH₃ | CH₃ | |
| OC₂H₅ | 3-Br | CH₃ | OH | OCH₃ | OCH₃ | |
| O—i-C₃H₇ | H | H | EtOCO₂ | OCH₃ | CH₃ | |
| O—n-C₃H₇ | H | H | n-C₃H₇CO₂ | CH₃ | OCH₃ | |

TABLE 2B-continued

| R5 | R6 | R | R' | X | Y | m.p. (°C.) |
|---|---|---|---|---|---|---|
| O—n-C3H7 | 6-CH3 | H | OH | CH3 | CH3 | |
| O—i-C4H9 | 3-CF3 | H | CH3OCO2 | OCH3 | OCH3 | |
| O—i-C4H9 | 5-CF3 | H | OH | OCH3 | CH3 | |
| CO2CH3 | 3-CF3 | H | OH | CH3 | CH3 | |
| CO2CH3 | 5-CF3 | H | OH | OCH3 | OCH3 | |
| CO2CH3 | H | H | CH3OCO2 | OCH3 | OC2H5 | |
| SO2N(CH3)2 | 6-SCH3 | H | OH | OCH3 | OCH3 | |
| SO2N(CH3)2 | 5-SCH3 | H | CH3CO2 | CH3 | CH3 | |
| SO2N(CH3)2 | 6-OCH3 | H | OH | CH3 | OCH3 | |
| SO2N(CH3)2 | H | H | (CH3)2NCO2 | OCH3 | OCH3 | |
| SO2N(CH3)2 | 3-OCH3 | H | OH | OCH3 | OCH2CH3 | |
| SO2N(CH3)2 | H | H | CH3NHCO2 | CH3 | CH(OCH2CH2O) | |
| SO2N(CH2CH3)2 | 3-CH3 | CH3 | OH | CH3 | C2H5 | |
| SO2N(CH2CH3)2 | 5-CH3 | H | n-C3H7CO2 | OCH3 | OC2H5 | |
| SO2N(CH2CH3)2 | 6-Cl | H | OH | OCH3 | CH3 | |
| CO2CH2CH3 | H | H | CF3CO2 | CH3 | OCH3 | |
| CO2CH2CH3 | 5-Cl | H | C2H5OCO2 | CH3 | CH(OCH3)2 | |
| CO2CH3 | 6-Cl | H | OH | CH3 | CH3 | |
| CO2CH3 | H | H | C2H5CO2 | CH3 | OCH3 | |
| CO2CH3 | 5-F | H | OH | CH3 | CH2OCH3 | |
| CO2—i-C3H7 | 5-F | H | OH | CH3 | CH3 | |
| CO2—i-C3H7 | 3-Br | CH3 | OH | OCH3 | OCH3 | |
| SO2N(OCH3)CH3 | H | H | Et2NCO2 | OCH3 | CH3 | |
| CO2CH2CH2OCH3 | H | H | n-C3H7OCO2 | OCH3 | OCH3 | |
| CO2CH2CH=CH2 | 6-CH3 | H | OH | CH3 | CH3 | |
| CO2CH2CH2Cl | H | H | CH3OCO2 | OCH3 | OCH3 | |
| CO2—n-C4H9 | H | H | C2H5CO2 | OCH3 | CH3 | |
| SO2CH3 | 3-CF3 | H | OH | CH3 | CH3 | |
| SO2CH3 | 5-CF3 | H | OH | CH3 | OCH3 | |
| SO2CH3 | H | H | CH3OCO2 | OCH3 | OC2H5 | |
| SO2CH3 | 6-SCH3 | H | OH | OCH3 | OCH3 | |
| SO2CH2CH=CH2 | 5-SCH3 | H | OH | CH3 | CH3 | |
| SO2CH2CH=CH2 | 6-OCH3 | H | (CH3)2NCO2 | CH3 | OCH3 | |
| SO2CH2CH2CH3 | H | H | OH | OCH3 | CH3 | |
| SCH2CH3 | 3-OCH3 | H | OH | OCH3 | OCH3 | |
| SCF3 | H | H | CH3NHCO2 | CH3 | CH(OCH2CH2O) | |
| SO2CHF2 | 3-CH3 | CH3 | OH | CH3 | C2H5 | |
| CH3 | 5-CH3 | H | C2H5OCO2 | OCH3 | OC2H5 | |
| i-C3H7 | 6-Cl | H | OH | OCH3 | CH3 | |
| n-C4H9 | H | H | n-C3H7OCO2 | CH3 | OCH3 | |
| OSO2N(CH3)2 | 6-Cl | H | C2H5CO2 | CH3 | CH3 | |
| OSO2N(CH3)2 | H | H | n-C3H7CO2 | CH3 | OCH3 | |
| OSO2CH(CH3)2 | 5-F | H | OH | CH3 | CH2OCH3 | |
| OSO2CH3 | 3-Br | CH3 | C2H5NHCO2 | OCH3 | OCH3 | |
| OSO2CH3 | H | H | (C2H5)2NCO2 | OCH3 | CH3 | |
| CH2OCH3 | H | H | CH3CO2 | CH3 | OCH3 | |
| CH2CH2OCH3 | 6-CH3 | H | OH | CH3 | CH3 | |
| OCF3 | H | H | C2H5OCO2 | OCH3 | OCH3 | |
| SO2—i-C3H7 | H | H | n-C3H7NHCO2 | OCH3 | CH3 | |
| CH2CH2OC2H5 | H | H | OH | OCH3 | CH3 | |
| C6H5 | 6-Cl | H | OCH3 | OCH3 | OCH3 | |
| C6H5 | 6-Cl | H | OCH3 | OCH3 | CH3 | |
| C6H5 | 6-OCH3 | H | OCH3 | OCH3 | OCH3 | |
| C6H5 | 6-OCH3 | H | OCH3 | OCH3 | CH3 | |

**Data refer to characteristic signals in NMR spectrum (CDCl3) in ppm downfield form tetramethylsilane.

TABLE 2c

| R' | R | R5 | R6 | X | Y | Z | m.p. (°C.) |
|---|---|---|---|---|---|---|---|
| OH | H | OCH2CH2OCH3 | H | CH3 | H | CH | |

TABLE 2c-continued

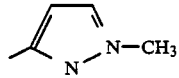

| R' | R | R5 | R6 | X | Y | Z | m.p. (°C.) |
|---|---|---|---|---|---|---|---|
| OH | H | OCH2CH=CH2 | H | CH3 | CH3 | N | |
| OH | H | OCH2CH≡CH | 6-OCH3 | CH3 | CH3 | CH | |
| OH | H | C6H5 | H | CH3 | CH3 | N | |
| OH | H | 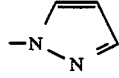 | H | CH3 | OCH3 | CH | |
| OH | H | 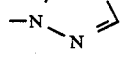 | H | OCH3 | OCH3 | N | |
| OH | H | Cl | H | OCH3 | OCH2C≡CH | N | |
| CONHCH3 | H | Cl | H | OCH3 | OCH2CF3 | CH | |
| OH | H | Cl | H | OCH3 | OCH2CH2OCH3 | N | |
| OH | H | Cl | H | OCH3 | CH2SCH3 | CH | |
| OH | H | F | H | OCH3 | OCF2H | CH | |
| OH | H | F | H | OCH3 | SCF2H | CH | |
| OH | H | F | 3-OCF2H | OCH3 | C(CH3)(OCH3)2 | CH | |
| OH | H | F | H | OCH3 | CF3 | N | |
| OH | H | Br | H | OCH3 | N(CH3)2 | CH | |
| OH | CH3 | Br | H | OCH3 | C(CH3)(SCH3)2 | N | |
| OH | CH3 | Br | H | OCF2H | CH(SCH2CH2S) | CH | |
| OH | CH3 | Br | H | CF3 | CH2CH3 | CH | |
| OH | CH3 | Br | H | F | OCH3 | CH | |
| OH | CH3 | Br | H | OC2H5 | C(CH3)(OCH2CH2O) | CH | |
| OH | H | 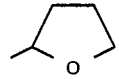 | H | CH3 | H | CH | |
| OH | H | -N(pyrazolyl) | H | CH3 | CH3 | CH | |
| OH | H | -N(triazolyl) | H | CH3 | OCH3 | CH | |
| COCF3 | H | O—n-C3H7 | H | OCH3 | OCH3 | CH | |
| OH | H | O—n-C3H7 | H | OCH3 | OCH2CH=CH2 | CH | |
| OH | H | O—n-C3H7 | H | OCH3 | OCH2C≡CH | N | |
| OH | H | OCH3 | 5-Br | OCH3 | OCH2CF3 | N | |
| OH | H | OCH3 | H | OCH3 | OCH2CH2OCH3 | N | |
| OH | H | OCH3 | H | OCH3 | CH2SCH3 | CH | |
| OH | H | NO2 | H | OCH3 | OCF2H | CH | |
| OH | H | NO2 | H | OCH3 | SCF2H | CH | |
| OH | H | NO2 | H | OCH3 | C(CH3)(OCH3)2 | CH | |
| OH | H | CF3 | H | OCH3 | CF3 | CH | |
| OH | H | CF3 | H | OCH3 | N(CH3)2 | CH | |
| OH | CH3 | CF3 | H | OCH3 | C(CH3)(SCH3)2 | CH | |
| OH | CH3 | CO2CH3 | H | OCF2H | CH(SCH2CH2S) | CH | |
| OH | CH3 | CO2CH3 | H | CF3 | CH2CH3 | CH | |
| OH | CH3 | CO2CH3 | H | F | OCH3 | CH | |
| OH | CH3 | CO2CH3 | H | OC2H5 | C(CH3)(OCH2CH2O) | CH | |
| OH | H | 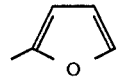 | H | CH3 | H | N | |
| OH | H | 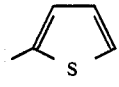 (furyl) | H | CH3 | CH3 | N | |
| OH | H | (thienyl) | H | CH3 | OCH3 | CH | |

TABLE 2c-continued

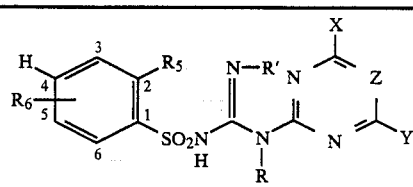

| R' | R | R5 | R6 | X | Y | Z | m.p. (°C.) |
|---|---|---|---|---|---|---|---|
| OH | H | CO2CH2CH=CH2 | H | OCH3 | OCH3 | CH | |
| OH | H | CO2CH2CH=CH2 | H | OCH3 | OCH2CH=CH2 | CH | |
| OH | H | CO2CH2CH=CH2 | H | OCH3 | OCH2C≡CH | N | |
| OH | H | SO2N(CH3)2 | H | OCH3 | OCH2CF3 | N | |
| OH | H | SO2N(CH3)2 | H | OCH3 | OCH2CH2OCH3 | N | |
| OH | H | SO2N(CH3)2 | H | OCH3 | CH2SCH3 | N | |
| OH | H | SO2N(OCH3)CH3 | H | OCH3 | OCF2H | CH | |
| OH | H | SO2N(CH3)C2H5 | H | OCH3 | SCF2H | CH | |
| OH | H | SCF3 | H | OCH3 | C(CH3)(OCH3)2 | CH | |
| OH | H | SO2CHF2 | H | OCH3 | CF3 | CH | |
| OH | H | CO2CH2CH2Cl | H | OCH3 | N(CH3)2 | CH | |
| OH | CH3 | CO2CH2CH3 | H | OCH3 | C(CH3)(SCH3)2 | CH | |
| OH | H | CO2CH2CH3 | H | OCF2H | CH(SCH2CH2S) | CH | |
| OH | H | CO2CH2CH3 | H | CF3 | CH2CH3 | CH | |
| OH | H | SO2CH3 | H | F | OCH3 | CH | |
| OCO—i-C3H7 | H | SO2CH3 | H | OC2H5 | C(CH3)(OCH2CH2O) | CH | |
| OH | H | (5-methyl-isoxazol-3-yl) | H | CH3 | H | N | |
| OH | H | (3-methyl-isoxazol-5-yl) | H | CH3 | CH3 | N | |
| OH | H | (4-methyl-1,2,3-thiadiazol-5-yl) | 6-OCF2H | CH3 | OCH3 | CH | |
| OH | H | (4-methyl-isoxazol-3-yl) | H | OCH3 | OCH3 | CH | |
| OH | H | OCH3 | H | OCH3 | OCH2C≡CH | CH | |
| OH | H | OCH3 | H | OCH3 | OCH2CF3 | CH | |
| OH | H | OCH3 | H | OCH3 | OCH2CH2OCH3 | CH | |
| OH | H | OC2H5 | H | OCH3 | CH2SCH3 | CH | |
| OH | H | OC2H5 | 3-F | OCH3 | OCF2H | CH | |
| OCO2CH2CH3 | H | OC2H5 | H | OCH3 | SCF2H | CH | |
| OH | H | CH3 | H | OCH3 | C(CH3)(OCH3)2 | N | |
| OH | H | CH3 | H | OCH3 | CF3 | N | |
| OH | H | CH3 | H | OCH3 | N(CH3)2 | N | |
| OH | CH3 | i-C3H7 | H | OCH3 | C(CH3)(SCH3)2 | CH | |
| OH | H | i-C3H7 | H | OCF2H | CH(SCH2CH2S) | CH | |
| OH | H | i-C3H7 | H | CF3 | CH2CH3 | CH | |
| OH | H | i-C3H7 | H | F | OCH3 | CH | |
| OH | H | n-C4H9 | H | OC2H5 | C(CH3)(OCH2CH2O) | N | |

TABLE 3

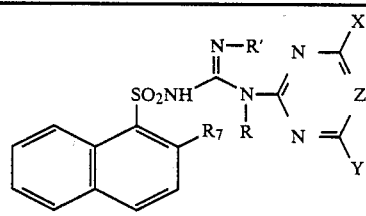

| R7 | R | R' | X | Y | Z | m.p. (°C.) |
|---|---|---|---|---|---|---|
| OH | H | OH | CH3 | CH3 | CH | |
| CH3 | H | OCON(CH3)2 | OCH3 | CH3 | N | |
| OCH3 | H | OH | Cl | CH3 | CH | |

TABLE 3-continued

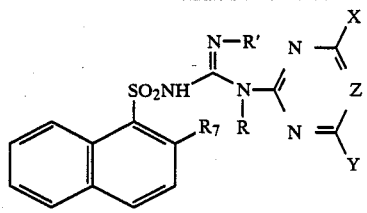

| R₇ | R | R' | X | Y | Z | m.p. (°C.) |
|---|---|---|---|---|---|---|
| F | H | OH | CH₃ | CH₃ | CH | |
| Cl | H | OH | OCH₃ | OCH₃ | CH | |
| Br | H | OH | F | OCH₃ | CH | |
| SO₂N(CH₃)₂ | H | OH | CH₃ | OCH₃ | CH | |
| OSO₂CH₃ | H | OH | OCF₂H | OCH₃ | CH | |
| SO₂CH₃ | H | OH | CH₂F | OC₂H₅ | CH | |
| OH | CH₃ | OH | OCH₂CH₃ | CH₂OCH₃ | N | |
| CH₃ | H | OH | CF₃ | N(CH₃)₂ | CH | |
| OCH₃ | H | OH | OCH₃ | CF₃ | CH | |
| F | H | OCO₂CH₂CH₃ | CH₃ | CH(OCH₃)₂ | CH | |
| Cl | H | OH | OCH₃ | OCF₂H | N | |
| Br | H | OH | OCH₃ | OCH₂CH₂OCH₃ | N | |
| SO₂N(CH₃)₂ | H | OH | OCH₃ | CH₂SCH₃ | N | |
| OSO₂CH₃ | H | OH | OCH₃ | OCH₂C≡CH | CH | |
| SCH₃ | H | OH | OCH₂CH₃ | 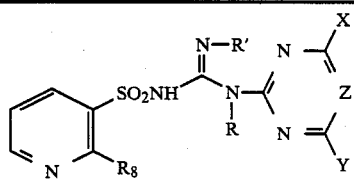 | CH | |
| SCH₃ | H | OH | CH₃ | | CH | |
| CH₃ | H | OH | CH₃ | OCH₃ | N | |
| OH | H | OH | CH₃ | OCH₃ | N | |

TABLE 4

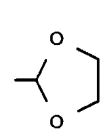

| R₈ | R | R' | X | Y | Z | m.p. (°C.) |
|---|---|---|---|---|---|---|
| CH₃ | H | OCON(CH₃)₂ | OCH₃ |  | N | |
| CH₂CH₃ | H | OH | Cl | OCH₃ | CH | |
| OCH₃ | H | OH | CH₃ | CH₂OC₂H₅ | CH | |
| OCH₂CH₃ | H | OH | OCH₃ | CH₃ | CH | |
| F | H | OH | F | CH₃ | CH | |
| Cl | H | OH | CH₃ | CH₃ | CH | |
| Br | H | OH | OCF₂H | CH₃ | CH | |
| SO₂N(CH₂CH₃)₂ | H | OH | CH₂F | OCH₃ | CH | |
| SO₂N(CH₃)₂ | CH₃ | OH | OCH₂CH₃ | OCH₃ | N | |
| SO₂N(OCH₃)CH₃ | H | OH | CF₃ | OCH₃ | CH | |
| SCH₂CH=CH₂ | H | OH | OCH₃ | OCH₃ | CH | |
| SO₂C₂H₅ | H | OCO₂CH₂CH₃ | CH₃ | OCH₃ | CH | |
| S—n-C₃H₇ | H | OH | OCH₃ | C₂H₅ | N | |
| SO₂CH₃ | H | OH | OCH₃ | OC₂H₅ | N | |
| SCH₃ | H | OH | OCH₃ | SCF₂H | N | |
| CH₃ | H | OH | OCH₃ | C(CH₃)(SCH₃)₂ | CH | |
| F | H | OH | OCH₂CH₃ | OCF₂H | CH | |
| Cl | H | OH | CH₃ | CH(OC₂H₅)₂ | CH | |
| Br | H | OH | CH₃ | CH₃ | N | |
| OCH₃ | H | OH | CH₃ | CH₃ | N | |

TABLE 5

| L | R₉ | R | R' | X | Y | Z | m.p. (°C.) |
|---|---|---|---|---|---|---|---|
| L₄ | CH₃ | H | OH | CH₃ | OCH₃ | CH | |
| L₄ | F | H | OCON(CH₃)₂ | OCH₃ | OCH₃ | N | |
| L₄ | NO₂ | H | OH | Cl | OCH₃ | CH | |
| L₄ | CO₂C₂H₅ | H | OH | CH₃ | OCH₃ | CH | |
| L₄ | SO₂N(CH₃)₂ | H | OH | OCH₃ | CH₂SCH₃ | CH | |
| L₄ | S—i-C₃H₇ | H | OH | F | CH₃ | CH | |
| L₅ | n-C₃H₇ | H | OH | CH₃ | N(CH₃)₂ | CH | |
| L₅ | Cl | H | OH | OCF₂H | CH₂OCH₃ | CH | |
| L₅ | Br | H | OH | CH₂F | CH₂OCH₃ | CH | |
| L₅ | CO₂CH₃ | CH₃ | OH | OCH₂CH₃ | CH₂OCH₃ | N | |
| L₅ | SO₂N(C₂H₅)₂ | H | OH | CF₃ | CH₃ | CH | |
| L₅ | SO₂N(OCH₃)CH₃ | H | OH | OCH₃ | CH₃ | CH | |
| L₅ | SO₂C₂H₅ | H | OCO₂CH₂CH₃ | CH₃ | CH₃ | CH | |
| L₅ | SCH₂CH=CH₂ | H | OH | OCH₃ | CH₃ | N | |
| L₅ | SO₂CH₃ | H | OH | OCH₃ | (dithiolane) | N | |
| L₆ | F | H | OH | OCH₃ | CH(OCH₃)₂ | CH | |
| L₆ | CO₂—i-C₃H₇ | H | OH | OCH₂CH₃ | OCH₃ | CH | |
| L₆ | SO₂CH₃ | H | OH | CH₃ | OCH₃ | CH | |
| L₆ | SO₂N(CH₃)₂ | H | OH | CH₃ | OCH₃ | N | |
| L₆ | Br | H | OH | CH₃ | OCH₃ | N | |

TABLE 6

| R₁₀ | R | R' | X | Y | Z | m.p. (°C.) |
|---|---|---|---|---|---|---|
| Cl | H | OH | CH₃ | CH₃ | CH | |
| NO₂ | H | OCON(CH₃)₂ | OCH₃ | CH₃ | N | |
| CO₂CH₃ | H | OH | Cl | CH₃ | CH | |
| CO₂CH₂CH₃ | H | OH | CH₃ | CH₃ | CH | |
| SO₂N(CH₃)₂ | H | OH | OCH₃ | CH₃ | CH | |
| OSO₂CH₃ | H | OH | F | OCH₃ | CH | |
| SO₂CH₃ | H | OH | CH₃ | OCH₃ | CH | |
| SO₂CH₂CH₃ | H | OH | OCF₂H | OCH₃ | CH | |
| OCH₃ | H | OH | CH₂F | OCH₃ | CH | |
| OCH₂CH₃ | CH₃ | OH | OCH₂CH₃ | OCH₃ | N | |
| OCH₂CH₃ | H | OH | CF₃ | CH₂SCH₃ | CH | |
| OCH₂CH₃ | H | OH | OCH₃ | CF₃ | CH | |
| OCH₃ | H | OCO₂CH₂CH₃ | CH₃ | CH₂CH₃ | CH | |
| SO₂CH₂CH₃ | H | OH | OCH₃ | OCH₃ | N | |
| SO₂CH₃ | H | OH | OCH₃ | SCF₂H | N | |
| OSO₂CH₃ | H | OH | OCH₃ | CH₃ | N | |
| CO₂CH₂CH₃ | H | OH | OCH₃ | CH₃ | CH | |
| CO₂CH₃ | H | OH | OCH₂CH₃ | CH₃ | CH | |
| CO₂CH₃ | H | OH | CH₃ | CH₃ | CH | |
| CO₂CH₃ | H | OH | CH₃ | OCH₃ | N | |
| NO₂ | H | OH | CH₃ | OCH₃ | N | |

TABLE 7

| $Q_1$ | $R_{11}$ | $R_{12}$ | $R_{13}$ | R | R' | X | Y | Z | m.p. (°C.) |
|---|---|---|---|---|---|---|---|---|---|
| O | H | H | H | H | OH | $CH_3$ | $OCH_3$ | CH | |
| S | H | H | H | H | $OCON(CH_3)_2$ | $OCH_3$ | $OCH_3$ | N | |
| $SO_2$ | H | H | H | H | OH | Cl | $OCH_3$ | CH | |
| NH | H | H | H | H | OH | $CH_3$ | $OCH_3$ | CH | |
| $NCH_3$ | H | H | H | H | OH | $OCH_3$ | $CH_3$ | CH | |
| O | $CH_3$ | $CH_3$ | H | H | OH | F | $CH_3$ | CH | |
| S | $CH_3$ | $CH_3$ | H | H | OH | $CH_3$ | $CH_3$ | CH | |
| $SO_2$ | $CH_3$ | $CH_3$ | H | H | OH | $OCF_2H$ | $CH_3$ | CH | |
| NH | $CH_3$ | $CH_3$ | H | H | OH | $CH_2F$ | $OCH_2CH_3$ | CH | |
| $NCH_3$ | $CH_3$ | $CH_3$ | $CH_3$ | $CH_3$ | OH | $OCH_2CH_3$ | $OCH_2CH_3$ | N | |
| O | $CH_2CH_3$ | $CH_3$ | H | H | OH | $CF_3$ | $OCH_2CH_3$ | CH | |
| S | $CH_2CH_3$ | $CH_3$ | H | H | OH | $OCH_3$ | $CF_3$ | CH | |
| $SO_2$ | $CH_2CH_3$ | $CH_2CH_3$ | H | H | $OCO_2CH_2CH_3$ | $CH_3$ | $OCF_2H$ | CH | |
| NH | $CH_2CH_3$ | $CH_3$ | H | H | OH | $OCH_3$ | $OCH_3$ | N | |
| $NCH_3$ | $CH_2CH_3$ | $CH_3$ | H | H | OH | $OCH_3$ | $OCH_3$ | N | |
| O | H | $CH_3$ | H | H | OH | $OCH_3$ | $OCH_3$ | N | |
| S | H | $CH_3$ | H | H | OH | $OCH_3$ | $OCH_3$ | CH | |
| $SO_2$ | H | $CH_3$ | H | H | OH | $OCH_2CH_3$ | $OCH_3$ | CH | |
| NH | H | $CH_3$ | H | H | OH | $CH_3$ | $C(CH_3)(OCH_3)_2$ | CH | |
| $NCH_3$ | H | $CH_3$ | H | H | OH | $CH_3$ | $CH_3$ | N | |
| O | $CH_3$ | $CH_3$ | H | H | OH | $CH_3$ | $CH_3$ | N | |

TABLE 8

| $Q_2$ | $R_{14}$ | $R_{15}$ | R | R' | X | Y | Z | m.p. (°C.) |
|---|---|---|---|---|---|---|---|---|
| O | H | H | H | OH | $CH_3$ | $CH_3$ | CH | |
| O | H | $CH_3$ | H | $OCON(CH_3)_2$ | $OCH_3$ | $CH_3$ | N | |
| O | H | H | H | OH | Cl | $CH_3$ | CH | |
| O | H | $CH_3$ | H | OH | $CH_3$ | $CH_3$ | CH | |
| O | $CH_3$ | H | H | OH | $OCH_3$ | $CH(OCH_3)_2$ | CH | |
| O | $CH_3$ | $CH_3$ | H | OH | F | $OCH_3$ | CH | |
| O | $CH_3$ | H | H | OH | $CH_3$ | $OCH_3$ | CH | |
| S | H | $CH_3$ | H | OH | $OCF_2H$ | $OCH_3$ | CH | |
| S | H | H | H | OH | $CH_2F$ | $OCH_3$ | CH | |
| S | H | $CH_3$ | $CH_3$ | OH | $OCH_2CH_3$ | $CH_2SCH_3$ | N | |
| S | H | H | H | OH | $CF_3$ | $OCH_2CH_3$ | CH | |
| S | $CH_3$ | $CH_3$ | H | OH | $OCH_3$ | $OCH_3$ | CH | |
| S | $CH_3$ | H | H | $OCO_2CH_2CH_3$ | $CH_3$ | $OCH_3$ | CH | |
| S | $CH_3$ | $CH_3$ | H | OH | $OCH_3$ | $OCH_3$ | N | |
| NH | H | H | H | OH | $OCH_3$ | $OCH_3$ | N | |
| NH | $CH_3$ | $CH_3$ | H | OH | $OCH_3$ | $OCH_3$ | N | |
| NH | H | H | H | OH | $OCH_3$ | $OCH_3$ | CH | |
| $NCH_3$ | H | $CH_3$ | H | OH | $OCH_2CH_3$ | $CH_3$ | CH | |
| $NCH_3$ | $CH_3$ | H | H | OH | $CH_3$ | $CH_3$ | CH | |
| $NCH_3$ | $CH_3$ | $CH_3$ | H | OH | $CH_3$ | $CH_3$ | N | |
| $NCH_3$ | $CH_3$ | H | H | OH | $CH_3$ | $CH_3$ | N | |

TABLE 9

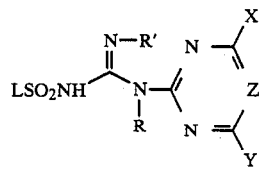

| L | m | R13 | R16 | R | R' | X | Y | Z | m.p. (°C.) |
|---|---|---|---|---|---|---|---|---|---|
| L-10 | 0 | H | CH3 | H | OH | CH3 | CH3 | CH | |
| L-10 | 1 | H | CH3 | H | OCON(CH3)2 | OCH3 | CH3 | N | |
| L-10 | 0 | H | CH3 | H | OH | Cl | CH3 | CH | |
| L-11 | 0 | CH3 | — | H | OH | CH3 | CH3 | CH | |
| L-11 | 0 | CH3 | — | H | OH | OCH3 | CH(OCH3)2 | CH | |
| L-11 | 0 | CH3 | — | H | OH | F | OCH3 | CH | |
| L-11 | 0 | H | — | H | OH | CH3 | OCH3 | CH | |
| L-12 | 1 | H | — | H | OH | OCF2H | OCH3 | CH | |
| L-12 | 0 | H | — | H | OH | CH2F | OCH3 | CH | |
| L-12 | 1 | H | — | CH3 | OH | OCH2CH3 | CH2SCH3 | N | |
| L-13 | 0 | CH3 | — | H | OH | CF3 | OCH2CH3 | CH | |
| L-13 | 1 | H | — | H | OH | OCH3 | OCH3 | CH | |
| L-13 | 0 | H | — | H | OCO2CH2CH3 | CH3 | OCH3 | CH | |
| L-13 | 1 | H | — | H | OH | OCH3 | OCH3 | N | |
| L-14 | 0 | H | — | H | OH | OCH3 | OCH3 | N | |
| L-14 | 1 | H | — | H | OH | OCH3 | OCH3 | N | |
| L-14 | 0 | CH3 | — | H | OH | OCH3 | OCH3 | CH | |
| L-10 | 1 | H | CH3 | H | OH | OCH2CH3 | CH3 | CH | |
| L-10 | 0 | H | C2H5 | H | OH | CH3 | CH3 | CH | |
| L-10 | 1 | H | C2H5 | H | OH | CH3 | CH3 | N | |
| L-10 | 0 | H | C2H5 | H | OH | CH3 | CH3 | N | |

TABLE 10

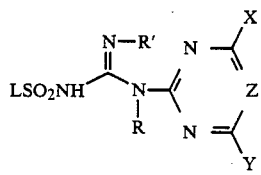

| L | R17 | R18 | R | R' | X | Y | Z | m.p. (°C.) |
|---|---|---|---|---|---|---|---|---|
| L15 | H | — | H | OH | CH3 | CH3 | CH | |
| L15 | H | — | H | OCON(CH3)2 | OCH3 | CH3 | N | |
| L15 | H | — | H | OH | Cl | CH3 | CH | |
| L15 | H | — | H | OH | CH3 | CH3 | CH | |
| L15 | H | — | H | OH | OCH3 | CH(OCH3)2 | CH | |
| L15 | H | — | H | OH | F | OCH3 | CH | |
| L15 | H | — | H | OH | CH3 | OCH3 | CH | |
| L15 | CH3 | — | H | OH | OCF2H | OCH3 | CH | |
| L15 | CH3 | — | H | OH | CH2F | OCH3 | CH | |
| L15 | CH3 | — | CH3 | OH | OCH2CH3 | CH2SCH3 | N | |
| L16 | CH3 | — | H | OH | CF3 | OCH2CH3 | CH | |
| L16 | CH3 | — | H | OH | OCH3 | OCH3 | CH | |
| L16 | CH3 | — | H | OCO2CH2CH3 | CH3 | OCH3 | CH | |
| L16 | CH3 | — | H | OH | OCH3 | OCH3 | N | |
| L16 | H | — | H | OH | OCH3 | OCH3 | N | |
| L16 | H | — | H | OH | OCH3 | OCH3 | N | |
| L16 | H | — | H | OH | OCH3 | OCH3 | CH | |
| L17 | CH3 | CH3 | H | OH | OCH2CH3 | CH3 | CH | |
| L17 | CH3 | H | H | OH | CH3 | CH3 | CH | |
| L17 | CH3 | CH3 | H | OH | CH3 | CH3 | N | |
| L17 | CH3 | CH3 | H | OH | CH3 | CH3 | N | |

TABLE 11

Structure: Phenyl ring with H at top, $R_6$ at left, $R_5$ ortho to $SO_2NH-C(=N-R')-N(R)-A$

| $R_5$ | $R_6$ | R | R' | A |
|---|---|---|---|---|
| $CH_3$ | H | H | OH | $A_2$: $Y_1 = CH_2$; $X_1 = CH_3$ |
| i-$C_3H_7$ | H | H | OH | $A_2$: $Y_1 = O$; $X_1 = OCH_3$ |
| $OC_2H_5$ | H | H | OH | $A_2$: $Y_1 = CH_2$; $X_1 = OCF_2H$ |
| O—n-$C_4H_9$ | H | H | OH | $A_3$: $X_1 = CH_3$ |
| F | 3-$CF_3$ | H | $OCO_2CH_3$ | $A_3$: $X_1 = OCH_2CH_3$ |
| Cl | H | H | $OCO_2CH_3$ | $A_4$: $X_1 = OCH_3$; $Y_2 = H$ |
| $NO_2$ | H | $CH_3$ | $OCO_2CH_3$ | $A_4$: $X_1 = CH_3$; $Y_2 = CH_3$ |
| $CF_3$ | H | H | $OCO_2CH_3$ | $A_5$: $X_2 = CH_3$; $Y_3 = OCH_3$ |
| $CO_2CH_3$ | H | H | $OCO_2CH_3$ | $A_5$: $X_2 = CH_3$; $Y_3 = SCH_3$ |
| $CO_2CH_2CH_3$ | 3-$CH_3$ | H | $OCO_2CH_3$ | $A_5$: $X_2 = CH_3$; $Y_3 = C_2H_5$ |
| $SO_2N(CH_3)_2$ | H | H | $OCO_2CH_3$ | $A_6$: $X_3 = CH_3$ |
| $SO_2N(C_2H_5)_2$ | H | H | $OCO_2CH_3$ | $A_6$: $X_3 = OCH_3$ |
| $OSO_2CH_2CH_3$ | H | $CH_3$ | $OCO_2CH_3$ | $A_2$: $Y_1 = O$; $X_1 = OCH_2CH_3$ |
| $SCH_3$ | 6-Cl | H | $OCO_2CH_3$ | $A_2$: $Y_1 = CH_2$; $X_1 = OCH_3$ |
| $SO_2CF_3$ | H | H | OH | $A_2$: $Y_1 = O$; $X_1 = CH_3$ |
| $OCHF_2$ | H | H | $OCOCH_3$ | $A_3$: $X_1 = OCF_2H$ |
| $OCH_2CH=CH_2$ | H | H | OH | $A_3$: $X_1 = OCH_3$ |
| $C_6H_5$ | H | H | OH | $A_4$: $X_1 = OCH_3$; $Y_2 = CH_3$ |
| 4-methyl-1,2,3-thiadiazol-5-yl | H | H | OH | $A_4$: $X_1 = OCF_2H$; $Y_2 = H$ |
| 5-methyl-furan-2-yl | — | H | OH | $A_5$: $X_2 = CH_2CF_3$; $Y_3 = CH_3$ |
| $CH_2OCH_3$ | H | H | OH | $A_6$: $X_3 = OCH_3$ |
| $CH_2OCH_3$ | H | H | OH | $A_6$: $X_3 = CH_3$ |

TABLE 12

Structure: $LSO_2NH-C(=N-R')-N(R)-A$

| L | R | R' | A |
|---|---|---|---|
| L-2: $R_7 = SO_2N(CH_3)_2$ | H | OH | $A_2$: $Y_1 = CH_2$; $X_1 = CH_3$ |
| L-2: $R_7 = OSO_2CH_3$ | H | OH | $A_2$: $Y_1 = O$; $X_1 = OCH_3$ |
| L-2: $R_7 = Cl$ | H | OH | $A_2$: $Y_1 = CH_2$; $X_1 = OCF_2H$ |
| L-2: $R_7 = Br$ | H | OH | $A_3$: $X_1 = CH_3$ |
| L-3: $R_8 = CH_3$ | H | $OCO_2CH_3$ | $A_3$: $X_1 = OCH_2CH_3$ |
| L-3: $R_8 = OCH_3$ | H | $OCO_2CH_3$ | $A_4$: $X_1 = OCH_3$; $Y_2 = H$ |
| L-3: $R_8 = SO_2CH_2CH_3$ | $CH_3$ | $OCO_2CH_3$ | $A_4$: $X_1 = CH_3$; $Y_2 = CH_3$ |
| L-4: $R_9 = CO_2CH_3$ | H | $OCO_2CH_3$ | $A_5$: $X_2 = CH_3$; $Y_3 = OCH_3$ |
| L-5: $R_9 = CO_2$-i-$C_3H_7$ | H | $OCO_2CH_3$ | $A_5$: $X_2 = CH_3$; $Y_3 = SCH_3$ |
| L-6: $R_9 = Cl$ | H | $OCO_2CH_3$ | $A_5$: $X_2 = CH_3$; $Y_3 = C_2H_5$ |
| L-4: $R_9 = NO_2$ | H | $OCO_2CH_3$ | $A_6$: $X_3 = CH_3$ |
| L-5: $R_9 = SO_2N(CH_3)_2$ | H | $OCO_2CH_3$ | $A_6$: $X_3 = OCH_3$ |
| L-6: $R_9 = C_2H_5$ | $CH_3$ | $OCO_2CH_3$ | $A_2$: $Y_1 = O$; $X_1 = OCH_2CH_3$ |
| L-7: $R_{10} = CO_2CH_3$ | H | $OCO_2CH_3$ | $A_2$: $Y_1 = CH_2$; $X_1 = OCH_3$ |
| L-7: $R_{10} = SO_2N(CH_3)_2$ | H | OH | $A_2$: $Y_1 = O$; $X_1 = CH_3$ |
| L-7: $R_{10} = OSO_2CH_3$ | H | $OCOCH_3$ | $A_3$: $X_1 = OCF_2H$ |
| L-8: $R_{11} = R_{12} = R_{13} = CH_3$; m = 0; $Q_1 = S$ | H | OH | $A_3$: $X_1 = OCH_3$ |
| L-9: $R_{14} = CH_3$; $R_{15} = H$; $Q_2 = NCH_3$ | H | OH | $A_4$: $X_1 = OCH_3$; $Y_2 = CH_3$ |
| L-10: $R_{16} = C_2H_5$; $R_{13} = H$; M = 1 | H | OH | $A_4$: $X_1 = OCF_2H$; $Y_2 = H$ |
| L-11: $R_{13} = H$; m = 0 | H | OH | $A_5$: $X_2 = C_2H_5$; $Y_3 = OC_2H_5$ |
| L-12: $R_{13} = CH_3$; m = 0 | H | OH | $A_5$: $X_2 = CH_2CF_3$; $Y_3 = CH_3$ |
| L-13: $R_{13} = CH_3$; m = 0 | H | OH | $A_5$: $X_2 = CH_3$; $Y_3 = C_2H_5$ |
| L-14: $R_{16} = CH_3$ | H | OH | $A_6$: $X_3 = OCH_3$ |
| L-15: $R_{17} = H$ | H | OH | $A_2$: $Y_1 = CH_2$; $X_1 = CH_3$ |
| L-15: $R_{17} = H$ | H | OH | $A_2$: $Y_1 = O$; $X_1 = OCH_3$ |
| L-15: $R_{17} = H$ | H | OH | $A_2$: $Y_1 = CH_2$; $X_1 = OCF_2H$ |
| L-16: $R_{17} = CH_3$ | H | OH | $A_3$: $X_1 = CH_3$ |
| L-16: $R_{17} = CH_3$ | H | $OCO_2CH_3$ | $A_3$: $X_1 = OCH_2CH_3$ |
| L-16: $R_{17} = CH_3$ | H | $OCO_2CH_3$ | $A_4$: $X_1 = OCH_3$; $Y_2 = H$ |
| L-17: $R_{17} = H$; $R_{18} = CH_3$ | $CH_3$ | $OCO_2CH_3$ | $A_4$: $X_1 = CH_3$; $Y_2 = CH_3$ |
| L-17: $R_{17} = H$; $R_{18} = CH_3$ | H | $OCO_2CH_3$ | $A_5$: $X_2 = CH_3$; $Y_3 = OCH_3$ |
| L-17: $R_{17} = H$; $R_{18} = CH_3$ | H | $OCO_2CH_3$ | $A_5$: $X_2 = CH_3$; $Y_3 = SCH_3$ |
| L-8: $R_{11} = R_{12} = R_{13} = 1$; H; m = 1; $Q_1 = SO_2$ | H | $OCO_2CH_3$ | $A_5$: $X_2 = CH_3$; $Y_3 = C_2H_5$ |
| L-8: $R_{11} = R_{12} = R_{13} = H$; m = 1; $Q_1 = SO_2$ | H | $OCO_2CH_3$ | $A_6$: $X_3 = CH_3$ |
| L-8: $R_{11} = R_{12} = R_{13} = H$; m = 1; $Q_1 = SO_2$ | H | $OCO_2CH_3$ | $A_6$: $X_3 = OCH_3$ |
| L-9: $R_{14} = R_{15} = H$; $Q_2 = S$ | $CH_3$ | $OCO_2CH_3$ | $A_2$: $Y_1 = O$; $X_1 = OCH_2CH_3$ |
| L-9: $R_{14} = R_{15} = H$; $Q_2 = S$ | H | $OCO_2CH_3$ | $A_2$: $Y_1 = CH_2$; $X_1 = OCH_3$ |
| L-9: $R_{14} = R_{15} = H$; $Q_2 = S$ | H | OH | $A_2$: $Y_1 = O$; $X_1 = CH_3$ |
| L-10: $R_{13} = R_{16} = CH_3$; m = 0 | H | $OCOCH_3$ | $A_3$: $X_1 = OCF_2H$ |
| L-10: $R_{13} = R_{16} = CH_3$; m = 0 | H | OH | $A_3$: $X_1 = OCH_3$ |
| L-10: $R_{13} = R_{16} = CH_3$; m = 0 | H | OH | $A_4$: $X_1 = OCH_3$; $Y_2 = CH_3$ |
| L-11: $R_{13} = CH_3$; m = 0 | H | OH | $A_4$: $X_1 = OCF_2H$; $Y_2 = H$ |
| L-11: $R_{13} = CH_3$; m = 0 | H | OH | $A_5$: $X_2 = C_2H_5$; $Y_3 = OC_2H_5$ |
| L-11: $R_{13} = CH_3$; m = 0 | H | OH | $A_5$: $X_2 = CH_2CF_3$; $Y_3 = CH_3$ |
| L-12: $R_{13} = H$; m = 1 | H | OH | $A_5$: $X_2 = CH_3$; $Y_3 = C_2H_5$ |
| L-13: $R_{13} = H$; m = 1 | H | OH | $A_6$: $X_3 = OCH_3$ |
| L-14: $R_{16} = H$ | H | OH | $A_6$: $X_3 = CH_3$ |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid diluent(s). More specifically, they will contain these ingredients in the following approximate proportions:

TABLE 13

| | Active Ingredient | Weight Percent* Diluent(s) | Surfactant(s) |
|---|---|---|---|
| Wettable Powders | 20–90 | 0–74 | 1–10 |
| Oil Suspensions, Emulsion, Solutions, (including Emulsifiable Concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, N.Y., 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., N.Y., 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff. and "Perry's Chemical Engineer's Handbook", 5th Ed., McGraw-Hill, N.Y., 1973, pp. 8–57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, Jun. 23, 1959, Col. 3, line 66 through Col. 5, line 17 and Examples 1–4;

G. C. Klingman, "Weed Control as a Science", John Wiley and Sons, Inc., N.Y., 1961, pp. 81–96; and J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

EXAMPLE 7

Wettable Powder

| | |
|---|---|
| 2-[[1-(4,6-dimethylpyrimidin-2-yl)amino]-1-(hydroxyimino)methyl]aminosulfonyl]benzoic acid, methyl ester | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended, and packaged.

EXAMPLE 8

Wettable Powder

| | |
|---|---|
| 2-[[1-(4-methoxy-6-methylpyrimidin-2-yl)amino]-1-(hydroxyimino)methyl]aminosulfonyl]benzoic acid, methyl ester | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE 9

Granule

| | |
|---|---|
| Wettable Powder of Example 8 | 5% |
| attapulgite granules (U.S.S. 20–40 mesh; 0.84–0.42 mm) | 95% |

A slurry of wettable powder containing ≈25% solids is sprayed on the surface of attapulgite granules in a double-cone blender. The granules are dried and packaged.

EXAMPLE 10

Extruded Pellet

| | |
|---|---|
| N',N'—dimethyl-N—[[1-(4,6-dimethyl-1,3,5-triazin-2-yl)amino]-1-(hydroxyimino)methyl]-1,2-benzenedisulfonamide | 25% |
| anhydrous sodium sulfate | 10% |

-continued

| | |
|---|---|
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 11

Oil Suspension

| | |
|---|---|
| N',N'—dimethyl-N—[[1-(4-methoxy-6-methylpyrimidin-2-yl)amino]-1-(hydroxyimino)methyl]-1,2-benzenedisulfonamide | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 12

Wettable Powder

| | |
|---|---|
| 2-[[1-(4,6-dimethylpyrimidin-2-yl)amino]-1-(hydroxyimino)methyl]aminosulfonyl]benzoic acid, methyl ester | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer-mill to produce particles essentially all below 100 microns, the material is reblended and sifted through a U.S.S. No. 50 sieve (0.3 mm opening) and packaged.

EXAMPLE 13

Low Strength Granule

| | |
|---|---|
| N',N'—dimethyl-N—[[1-(4,6-dimethyl-1,3,5-triazin-2-yl)-animo]-1-(hydroxyimino)methyl]-1,2-benzenedisulfonamide | 1% |
| N,N—dimethylformamide | 9% |
| attapulgit granules (U.S.S. 20–40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 14

Aqueous Suspension

| | |
|---|---|
| N',N'—dimethyl-N—[[1-(4-methoxy-6-methylpyrimidin-2-yl)amino]-1-(hydroxyimino)methyl]-1,2-benzenedisulfonamide | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 15

Solution

| | |
|---|---|
| 2-[[1-(4-methoxy-6-methylpyrimidin-2-yl)amino]-1-(hydroxyimino)methyl]aminosulfonyl]benzoic acid, methyl ester | 5% |
| water | 95% |

The salt is added directly to the water with stirring to produce the solution, which may then be packaged for use.

EXAMPLE 16

Low Strength Granule

| | |
|---|---|
| 2-[[1-(4,6-dimethylpyrimidin-2-yl)amino]-1-(hydroxyimino)methyl]aminosulfonyl]benzoic acid, methyl ester | 0.1% |
| attapulgite granules (U.S.S. 20–40 mesh) | 99.9% |

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 17

Granule

| | |
|---|---|
| 2-[[1-(4-methoxy-6-methylpyrimidin-2-yl)amino]-1-(hydroxyimino)methyl]aminosulfonyl]benzoic acid methyl ester | 80% |
| wetting agent | 1% |
| crude ligninsulfonate salt (containing 5–20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14–100 mesh (1410–1490microns), and packaged for use.

EXAMPLE 18

High Strength Concentrate

| | |
|---|---|
| N',N'—dimethyl-N—[[1-(4-methoxy-6-methylpyrimidin-2-yl)amino]-1-(hydroxyimino)methyl]-1,2-benzenedisulfonamide | 99% |
| silica aerogel | 0.5% |
| synthetic amorphous silica | 0.5% |

The ingredients are blended and ground in a hammer-mill to produce a material essentially all passing a U.S.S. No. 50 screen (0.3 mm opening). The concentrate may be formulated further if necessary.

EXAMPLE 19

Wettable Powder

| | |
|---|---|
| N',N'—dimethyl-N—[[1-(4,6-dimethyl-1,3,5-triazin-2-yl)-amino]-1-(hydroxyimino)methyl]-1,2-benzenedisulfonamide | 90% |
| dioctyl sodium sulfosuccinate | 0.1% |
| synthetic fine silica | 9.9% |

The ingredients are blended and ground in a hammer-mill to produce particles essentially all below 100 microns. The material is sifted through a U.S.S. No. 50 screen and then packaged.

EXAMPLE 20

Wettable Powder

| | |
|---|---|
| 2-[[1-(4,6-dimethylpyrimidin-2-yl)amino]-1-(hydroxyimino)methyl]aminosulfonyl]benzoic acid, methyl ester | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 21

Oil Suspension

| | |
|---|---|
| N',N'—dimethyl-N—[[1-(dimethyl-1,3,5-triazin-2-yl)-amino]-1-(hydroxyimino)methyl]-1,2-benzenedisulfonamide | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

EXAMPLE 22

Dust

| | |
|---|---|
| 2-[[1-(4-methoxy-6-methylpyrimidin-2-yl)amino]-1-(hydroxyimino)methyl]aminosulfonyl]benzoic acid methyl ester | 10% |
| attapulgite | 10% |
| Pyrophyllite | 80% |

The active ingredient is blended with attapulgite and then passed through a hammer-mill to produce particles substantially all below 200 microns. The ground concentrate is then blended with powdered pyrophyllite until homogeneous.

EXAMPLE 23

Emulsifiable Concentrate

| | |
|---|---|
| N',N'—dimethyl-N—[[1-(4-methoxy-6-methylpyrimidin-2-yl)amino]-1-(hydroxyimino)methyl]-1,2-benzenedisulfonamide | 20% |
| chlorobenzene | 74% |
| sorbitan monostearate and polyoxyethylene condensates thereof | 6% |

The ingredients are combined and stirred to produce a solution which can be emulsified in water for application.

Utility

The compounds of the present invention are active herbicides. They have utility for broad-spectrum pre- and/or post-emergence weed control in areas where complete control of all vegetation is desired, such as around fuel storage tanks, ammunition depots, industrial storage areas, parking lots, drivein theaters, around billboards, highway and railroad structures. Alternatively, the subject compounds are useful for the selective pre- or post-emergence weed control in crops, such as wheat and barley.

The rates of application for the compounds of the invention are determined by a number of factors, including their use as selective or general herbicides, the crop species involved, the types of weeds to be controlled, weather and climate, formulations selected, mode of application, amount of foliage present, etc. In general terms, the subject compounds should be applied at levels of around 0.03 to 5 kg/ha, the lower rates being suggested for use on lighter soils and/or those having a low organic matter content, for selective weed control or for situations where only short-term persistence is required.

The compounds of the invention may be used in combination with any other commercial herbicide examples of which are those of the triazine, triazole, uracil, urea, amide, diphenylether, carbamate and bipyridylium types.

The herbicidal properties of the subject compounds were discovered in a number of greenhouse tests. The test procedures and results follow.

Test A

Seeds of crabgrass (Digitaria spp.), barnyardgrass (Echinochloa crusgalli), wild oats (Avena fatua), sicklepod (Cassia obtusifolia), morningglory (Ipomoea spp.), cocklebur (Xanthium pensylvanicum), sorghum, corn, soybean, sugar beet, rice, wheat, and purple nutsedge (Cyperus rotundus) tubers were planted and treated pre-emergence with the test chemicals dissolved in a non-phytotoxic solvent. At the same time, these crop and weed species, along with cotton and bush bean, were treated with a soil/foliage application. At the time of treatment, the plants ranged in height from 2 to 18 cm. Treated plants and controls were maintained in a greenhouse for sixteen days, after which all species were compared to controls and visually rated for response to treatment. The ratings, summarized in Table A, are based on a numerical scale extending from 0=no injury, to 10=complete kill. The accompanying descriptive symbols have the following meanings:

C=chlorosis/necrosis;
E=emergence inhibition;
G=growth retardation;
H=formative effect;
U=unusual pigmentation; and
6Y=abscised buds or flowers.

Note that compounds tested are highly active herbicides at the low rates of application selected for this test.

Compounds

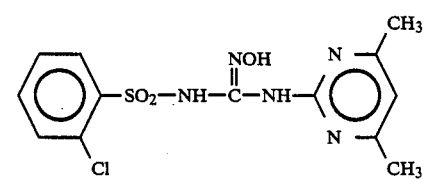
Compound 1

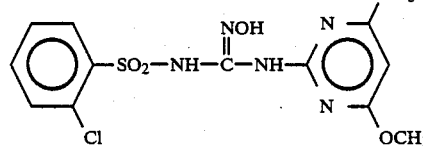
Compound 2

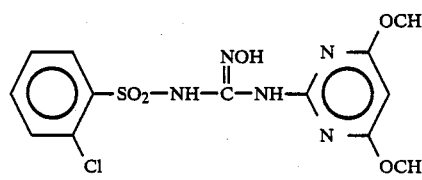
Compound 3

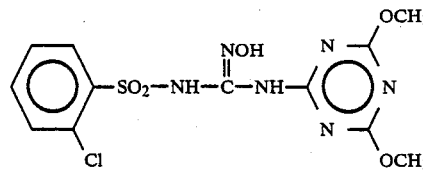
Compound 4

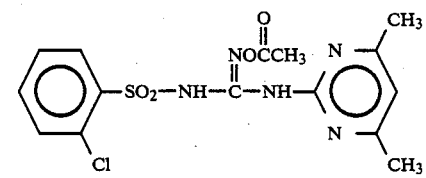
Compound 5

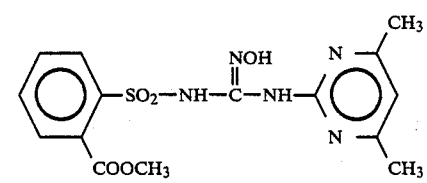
Compound 6

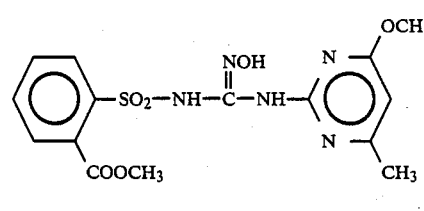
Compound 7

-continued
Compounds

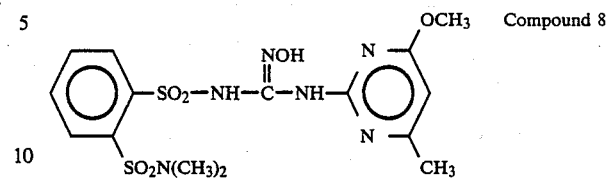
Compound 8

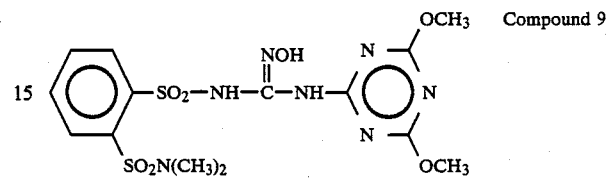
Compound 9

TABLE A

| Rate kg/ha | Cmpd. 1 .05 | Cmpd. 1 0.4 | Cmpd. 2 .05 | Cmpd. 3 .05 |
|---|---|---|---|---|
| POST-EMERGENCE | | | | |
| Bush bean | 3C,7H,6Y | 9C | 9C | 9C |
| Cotton | 5C,7H | 6C,9G | 4C,9G | 3C,9G |
| Morningglory | 3C | 4C,8G | 2C,9G | 3C,8H |
| Cocklebur | 3G | 8G | 3C,9G | 3C,8H |
| Sicklepod | 2C | 3C,8G | 2C,8G | 4C,9G |
| Nutsedge | 2C,6G | 10C | 4C,9G | 9C |
| Crabgrass | 0 | 2C,8G | 1C,3H | 2C,3G |
| Barnyardgrass | 2C,6H | 9C | 5C,9H | 2C,9H |
| Wild Oats | 1C | 1C,7G | 0 | 2C,4G |
| Wheat | 1C | 1C,9G | 0 | 3G |
| Corn | 2U,8H | 6U,9G | 3U,9G | 2U,9G |
| Soybean | 1C,3H | 4C,9G | 2C,9H | 3C,9H |
| Rice | 2C,8H | 5C,9G | 3C,9G | 4C,9G |
| Sorghum | 1U,9G | 5U,9G | 2C,9G | 2C,9G |
| Sugar beet | — | — | — | — |
| PRE-EMERGENCE | | | | |
| Morningglory | 3C | 8G | 9G | 9G |
| Cocklebur | 2C,7H | 8H | 9H | — |
| Sicklepod | 2C,5G | 3C,9G | 2C,8G | 9G |
| Nutsedge | 5G | 3C,9G | 2C,5G | 10E |
| Crabgrass | 0 | 3C | 1C,3G | 1C,5G |
| Barnyardgrass | 3C,6H | 3C,9H | 5C,9H | 9H |
| Wild Oats | 0 | 2C,7G | 5C,9G | 8G |
| Wheat | 3G | 2C,8G | 4C,9G | 2C,8G |
| Corn | 2C,6G | 1C,9G | 2C,9G | 2C,9H |
| Soybean | 2C | 3C,6G | 3C,8H | 7H |
| Rice | 4C,6G | 10E | 5C,9G | 10E |
| Sorghum | 2C,7H | 3C,9H | 4C,9G | 1C,9H |
| Sugar beet | — | — | — | — |

| Rate kg/ha | Cmpd. 4 .05 | Cmpd. 5 .05 | Cmpd. 6 .05 | Cmpd. 7 0.5 |
|---|---|---|---|---|
| POST-EMERGENCE | | | | |
| Bush bean | 1C | 5C,9G,6Y | 3C,6H,6Y | 9C |
| Cotton | 4C,8G | 4C,8H | 2C,5G | 6C,9G |
| Morningglory | 3C,8G | 3C,5G | 3G | 2C,7G |
| Cocklebur | 2C | 5G | 4G | 4C,9H |
| Sicklepod | 5c,9G | 1C | 3G | 9C |
| Nutsedge | 0 | 3C,8G | 7C,9G | 10C |
| Crabgrass | 3C | 2H | 10C | 4C,9G |
| Barnyardgrass | 2C,5H | 3C,8H | 4H | 9C |
| Wild Oats | 0 | 2C | 0 | 5C,9H |
| Wheat | 0 | 1C | 0 | 5C,9G |
| Corn | 2G | 3C,8H | 2C,8H | 5C,9G |
| Soybean | 3C,8G | 2C,7H | 2C,2H | 5C,9G |
| Rice | 3G | 3C,9H | 2C,8H | 5C,9G |
| Sorghum | 3G | 3C,9G | 2C,9H | 4U,9G |
| Sugar beet | — | — | 2C | 10C |
| PRE-EMERGENCE | | | | |
| Morningglory | 9G | 3C | 2C,4G | 8H |

TABLE A-continued

| | | | | |
|---|---|---|---|---|
| Cocklebur | 9H | 9H | 9H | 8H |
| Sicklepod | 9G | 3C,8H | 2C,5G | 2C,9G |
| Nutsedge | 9G | 3C,8G | 2C,5G | 10E |
| Crabgrass | 3G | 2C | 1C | 2C |
| Barnyardgrass | 2C,5G | 5C,9H | 2H | 4C,9H |
| Wild Oats | 1C | 2C,8G | 2C,8G | 3C,9G |
| Wheat | 1C | 3C,9G | 9G | 2C,9H |
| Corn | 2C,8G | 4C,9H | 9G | 3C,9H |
| Soybean | 8H | 3C,5H | 4C,7G | 3C,7H |
| Rice | 6G | 5C,9H | 3C,8H | 10E |
| Sorghum | 2C,5G | 4C,9H | 2C,9H | 2C,9G |
| Sugar beet | — | — | 2C,9G | 9C |

| | Cmpd. 8 | Cmpd. 9 |
|---|---|---|
| Rate kg/ha | .05 | .05 |
| POST-EMERGENCE | | |
| Bush bean | 5C,9G,6Y | 5C,9G,6Y |
| Cotton | 9C | — |
| Morningglory | 5C,9G | 5C,9G |
| Cocklebur | 4C,9G | 4C,9G |
| Sicklepod | 3C,8G | 4C,3H |
| Nutsedge | 2C,7G | 5G |
| Crabgrass | 2C,9G | 2C,8G |
| Barnyardgrass | 2C,9H | 5C,9H |
| Wild Oats | 2C,8G | 0 |
| Wheat | 5C,9G | 0 |
| Corn | 3U,9H | 9C |
| Soybean | 2C,9H | 9C |
| Rice | 5C,9G | 5C,9G |
| Sorghum | 2C,9G | 9C |
| Sugar beet | 3C,9G | 9C |
| PRE-EMERGENCE | | |
| Morningglory | 9C | 9C |
| Cocklebur | 9H | — |
| Sicklepod | 5C,9G | 2C,9G |
| Nutsedge | 10E | 6G |
| Crabgrass | 3C,9G | 2C,6G |
| Barnyardgrass | 4C,9H | 3C,9H |
| Wild Oats | 3C,9G | 3C,9G |
| Wheat | 10C | 1C,6G |
| Corn | 9G | 5C,9H |
| Soybean | 3C,9H | 9H |
| Rice | 10E | 10E |
| Sorghum | 5C,9H | 5C,9H |
| Sugar beet | 5C,9G | 9C |

Test B

Two plastic bulb pans were filled with fertilized and limed Woodstown sandy loam. One pan was planted with corn, sorghum, Kentucky bluegrass and several grass weeds. The other pan was planted with cotton, soybeans, purple nutsedge (*Cyperus rotundus*), and several broadleaf weeds. The following grass and broadleaf weeds were planted: crabgrass (*Digitaria sanguinalis*), barnyardgrass (*Echinochloa crusgalli*), wild oats (*Avena fatua*), johnsongrass (*Sorghum halepense*), dallisgrass (*Paspalum dilatatum*), giant foxtail (*Setaria faberii*), cheatgrass (*Bromus secalinus*), mustard (*Brassica arvensis*), cocklebur (*Xanthium pensylvanicum*), pigweed (*Amaranthus retroflexus*), morningglory (*Ipomoea hederacea*), sicklepod (*Cassia obtusifolia*), teaweed (*Sida spinosa*), velvetleaf (*Abutilon theophrasti*), and jimsonweed (*Datura stramonium*). A 12.5 cm diameter plastic pot was also filled with prepared soil and planted with rice and wheat. Another 12.5 cm pot was planted with sugar beets. The above four containers were treated preemergence with several test compounds within the scope of the invention.

Twenty-eight days after treatment, the plants were evaluated and visually rated for response to the chemical treatments utilizing the rating system described previously for Test A. The data are summarized in Table B.

TABLE B

PRE-EMERGENCE ON WOODSTOWN SANDY LOAM

| | Compound 1 | | Compound 2 | |
|---|---|---|---|---|
| Rate kg/ha | 0.120 | 0.500 | 0.030 | 0.120 |
| Crabgrass | 2G | 5G | 2G | 4G |
| Barnyardgrass | 8G,3H | 10C | 7G,3H | 9G,5H |
| Sorghum | — | — | 7G,5H | 9G,5H |
| Wild Oats | 2G | 5G | 4G | 5G |
| Johnsongrass | 5G,3H | 8G,3H | 4G,3H | 6G,2H |
| Dallisgrass | 6G | 8G,5H | 2G | 4G |
| Giant foxtail | 6G,5H | 8G,5H | 4G | 6G,3H |
| Ky. bluegrass | 8G,8C | 10C | 6G | 7G |
| Cheatgrass | 6G,3C | 10C | 8G,8C | 8G,9C |
| Sugar beets | 8G,8C | 10C | 8G,8C | 10C |
| Corn | 7G,5H | 9G,8H | 6G,3H | 7G,3H |
| Mustard | 9G,9C | 10C | 9G,8C | 9G,9C |
| Cocklebur | 6G | 7G,3H | 6G | 5G |
| Pigweed | 8G | 10C | — | — |
| Nutsedge | 7G | 10E | 7G | 7G |
| Cotton | 3G | 8G | 3G | 5G,3H |
| Morningglory | 0 | 6G,5H | 4G | 9G,5C |
| Sicklepod | 6G | 7G | 7G | 8G,3H |
| Teaweed | 5G | 8G,3H | 5G | 10C |
| Velvetleaf | 6G,5H | 9G,9C | 5G,5H | 8G,9C |
| Jimsonweed | 6G | 7G | 7G | 8G,8C |
| Soybean | 3G | 6G,5H | 3G,3H | 6G,5H |
| Rice | 9G,9C | 10C | 7G,8C | 10C |
| Wheat | 4G | 6G | 0 | 4G |

| | Compound 3 | | Compound 4 | |
|---|---|---|---|---|
| Rate kg/ha | 0.030 | 0.120 | 0.007 | 0.030 |
| Crabgrass | 0 | 6G | 0 | 0 |
| Barnyardgrass | 6G,2H | 8G,5H | 0 | 3G |
| Sorghum | 6G,3H | 9G,5H | 0 | 0 |
| Wild Oats | 3G | 6G | 0 | 0 |
| Johnsongrass | 4G,2H | 7G,5H | 0 | 0 |
| Dallisgrass | 0 | 5G | 0 | 0 |
| Giant foxtail | 3G | 7G,3H | 0 | 0 |
| Ky. bluegrass | 5G,3H | 7G,3H | 4G | 0 |
| Cheatgrass | 8G,8C | 8G,9C | 0 | 0 |
| Sugar beets | 10C | 10C | 6G | 8G |
| Corn | 5G,3H | 7G,3H | 2G | 3G |
| Mustard | 9G,5H | 9G,9C | 9G | 9G,9C |
| Cocklebur | 0 | 3G | 0 | 2G |
| Pigweed | 10E | 10E | — | — |
| Nutsedge | 9G,9E | 10E | 0 | 5G |
| Cotton | 2G | 4G | 2G | 5G |
| Morningglory | 3G | 3G | 0 | 7G |
| Sicklepod | 8G | 8G | 5G | 6G |
| Teaweed | 7G | 8G | 6G | 9G |
| Velvetleaf | 7G,5H | 9G,8C | 5G,5H | 8G |
| Jimsonweed | 5G | 6G | 0 | 4G |
| Soybean | 3G | 6G,5H | 5G | 8G |
| Rice | 8G,8C | 10E | 0 | 5G |
| Wheat | 2G | 4G | 0 | 0 |

| | Compound 5 | |
|---|---|---|
| Rate kg/ha | 0.030 | 0.120 |
| Crabgrass | 0 | 0 |
| Barnyardgrass | 2G | 3H,8G |
| Sorghum | 2G | 3H,8G |
| Wild Oats | 0 | 2G |
| Johnsongrass | 0 | 2H,4G |
| Dallisgrass | 4G | 8G |
| Giant foxtail | 3H,4G | 5H,8G |
| Ky. bluegrass | 6G | 10E |
| Cheatgrass | 5G | 8G |
| Sugar beets | 5G | 8G |
| Corn | 3G | 3H,7G |
| Mustard | 9G,9C | 9G,9C |
| Cocklebur | 2G | 2G |
| Pigweed | — | — |
| Nutsedge | 2G | 6G |
| Cotton | 3G | 5G |
| Morningglory | 2G | 2G |
| Sicklepod | 2G | 5G |
| Teaweed | 0 | 0 |
| Velvetleaf | 0 | 5G |
| Jimsonweed | 0 | 4G |
| Soybean | 3G | 3G |

TABLE B-continued

PRE-EMERGENCE ON
WOODSTOWN SANDY LOAM

| | | |
|---|---|---|
| Rice | 8G | 9G,9C |
| Wheat | 2G | 3G |

Test C

The test chemicals, dissolved in a non-phytotoxic solvent, were applied in an overall spray to the foliage and surrounding soil of selected plant species. One day after treatment, plants were checked for rapid burn injury. Approximately fourteen days after treatment all species were visually compared to untreated controls and rated for response to treatment. The rating system was as described previously for Test A. The data are presented in Table C.

All plant species were seeded in Woodstown sandy loam soil and grown in a greenhouse. The following species were grown in soil contained in plastic pots (25 cm diameter by 13 cm deep): soybeans, cotton, alfalfa, corn, rice, wheat, sorghum, velvetleaf (*Abutilon theophrasti*), sesbania (*Sesbania exaltata*), sicklepod (*Cassia obtusifolia*), morningglory (*Ipomoea hederacea*), jimsonweed (*Datura stramonium*), cocklebur (*Xanthium pensylvanicum*), crabgrass (Digitaria spp.), nutsedge (*Cyperus rotundus*), barnyardgrass (*Echinochloa crusgalli*), giant foxtail (*Setaria faberii*), and wild oats (*Avena fatua*). The following species were grown in soil in a paper cup (12 cm diameter by 13 cm deep): sunflower, sugar beets, and rape. All plants were sprayed approximately 14 days after planting. Additional plant species, such as johnsongrass and field bindweed, are sometimes added to this test in order to evaluate unusual selectivity.

TABLE C

Over-the-Top Soil/Foliage Treatment

| | Compound 2 | | Compound 5 | |
|---|---|---|---|---|
| Rate, kg/ha | 0.015 | 0.004 | 0.06 | 0.015 |
| Soybeans | 8G,6C | 6G | 3G | 0 |
| Velvetleaf | 0 | 0 | 4G | 0 |
| Sesbania | 0 | — | 0 | 0 |
| Sicklepod | 0 | 0 | 0 | 0 |
| Cotton | 3G | 3G | 3G | 3G |
| Morningglory | 2G | 0 | 4G | 3G |
| Alfalfa | 7G | 5G | 4G | 3G |
| Jimsonweed | 3G | 0 | 0 | 0 |
| Cocklebur | 0 | — | 2G | 3G |
| Sunflower | 2G | 0 | 3G | 1G |
| Rape | 2G | 0 | 5G | 0 |
| Sugar beets | 2G | 0 | — | — |
| Corn | 2G | 0 | 1C | 0 |
| Crabgrass | 4G | 0 | 0 | 0 |
| Rice | 6G | 2G | 6G | 6G |
| Nutsedge | 0 | 0 | 0 | 0 |
| Barnyardgrass | 0 | 3G | 0 | 0 |
| Wheat | 0 | 0 | 0 | 0 |
| Giant Foxtail | 2G | 4G | 0 | 0 |
| Wild Oats | 0 | 0 | 0 | 0 |
| Sorghum | 3G | 5G | 8G | 6G |
| Johnsongrass | 0 | 0 | 0 | 0 |
| Field Bindweed | 3G | 0 | 0 | 0 |

Test D

Two ten-inch in diameter plastic pans lined with polyethylene liners were filled with prepared Woodstown sandy loam soil. One pan was planted with seeds of wheat (*Triticum aestivum*), barley (*Hordeum vulgare*), wild oats (*Avena fatua*), downy brome (*Bromus tectorum*), cheatgrass (*Bromus secalinus*), blackgrass (*Alopecurus myosuroides*), annual bluegrass (*Poa annua*), green foxtail (*Setaria viridis*), quackgrass (*Agropyron repens*), Italian ryegrass (*Lolium multiflorum*) and ripgut brome (*Bromus rigidus*). The other pan was planted with seeds of Russian thistle (*Salsola kali*), tansy mustard (*Descuraina pinnata*), cleavers (*Galium aparine*), tumble mustard (*Sisymbrium altissium*), kochia (*Kochia scoparia*), shepherd's purse (*Capsella bursa-pastoris*), *Matricaria inodora*, black nightshade (*Solanum nigrum*), yellow rocket (*Barbarea vulgaris*), rapeseed (*Brassica napus*), and wild buckwheat (*Polygonum convolvulus*). The above two pans were treated preemergence. At the same time, two pans in which the above plant species were growing were treated postemergence. Plant height at the time of treatment ranged from 1–15 cm depending on plant species.

The compounds applied were diluted with a non-phytotoxic solvent and sprayed over the top of the pans. An untreated control and a solvent-alone control were included for comparison. All treatments were maintained in the greenhouse for 19–21 days at which time the treatments were compared to the controls and the effects visually rated. The recorded data are presented in Table D. Some of the compounds tested have utility for selective weed control in cereal crops such as wheat and barley.

TABLE D

| | Compound 2 | | | |
|---|---|---|---|---|
| | Pre-Emergence | | Post-Emergence | |
| Rate kg/ha | 0.060 | 0.015 | 0.060 | 0.015 |
| wheat | 7G | 2G | 6G | 3G |
| barley | 1C,7G | 2G | 6G | 3G |
| wild oats | 1C,7G | 5G | 5G | 2G |
| downy brome | 2C,9G | 8G | 8G | 7G |
| cheatgrass | 1C,9G | 8G | 8G | 7G |
| blackgrass | 2C,8G | 7G | 5G | 3G |
| annual bluegrass | 8G | 7G | 7G | 3G |
| green foxtail | 2C,8G | 2C,4G | 2C,8G | 4G |
| quackgrass | 9G | 8G | 8G | 6G |
| Italian ryegrass | 1C,8G | 7G | 4C,8G | 7G |
| ripgut brome | 8G | 8G | 2C,8G | 7G |
| Russian thistle | 2C,3G | 2G | 8C,8G | 4C,5G |
| tansy mustard | 2C,9G | 9G | 8C,8G | 5C,7G |
| Galium aparine | 6G | 8G | 7G | 4G |
| tumble mustard | 1C,8G | 9G | 10C | 7G |
| kochia | 7G | 5G | 3C,8G | 4G |
| shepherd's purse | 2C,9G | 9G | 4C,9G | 7G |
| *Matricaria inodora* | 7G | 7G | 8C,8G | 2C,7G |
| black nightshade | 8G | 5G | 6G | 6G |
| yellow rocket | 9G | 8G | 7G | 5G |
| rapeseed | 2C,9G | 9G | 10C | 2C,8G |
| wild buckwheat | 7G | 6G | 7G | 4G |

| | Compound 3 | | | |
|---|---|---|---|---|
| | Pre-Emergence | | Post-Emergence | |
| Rate kg/ha | 0.060 | 0.015 | 0.060 | 0.015 |
| wheat | 3G | 0 | 3G | 0 |
| barley | 3G | 0 | 5G | 0 |
| wild oats | 5G | 0 | 4G | 0 |
| downy brome | 9G | 8G | 9G | 7G |
| cheatgrass | 2C,9G | 7G | 8G | 6G |
| blackgrass | 7G | 6G | 6G | 3G |
| annual bluegrass | 7G | 6G | 2C,8G | 3G |
| green foxtail | 2C,6G | 3G | 2C,6G | 6G |
| quackgrass | 9G | 8G | 8G | 7G |
| Italian ryegrass | 8G | 8G | 2C,8G | 6G |
| ripgut brome | 8G | 6G | 7G | 6G |
| Russian thistle | 1C,2G | 0 | 8C,8G | 0 |
| tansy mustard | 9G | 9G | 10C | 9G |
| Galium aparine | 10E | 8G | 6G | 5G |
| tumble mustard | 2C,9G | 9G | 10C | 9G |
| kochia | 8G | 2C,5G | 2C,8G | 5G |
| shepherd's purse | 9C,9G | 9C,9G | 10C | 2C,8G |
| *Matricaria inodora* | 8G | 9G | 8C,8G | 8C,8G |
| black nightshade | 6G | 3G | 7G | 6G |
| yellow rocket | 9G | 7G | 8C,8G | 8C,8G |
| rapeseed | 3C,9G | 9G | 10C | 10C |

TABLE D-continued

| wild buckwheat | 6G | 4G | 2C,8G | 7G |
|---|---|---|---|---|
| | Compound 5 | | | |
| | Pre-Emergence | | Post-Emergence | |
| Rate kg/ha | 0.060 | 0.250 | 0.060 | 0.250 |
| wheat | 1C,2G | 5G | 2G | 7G |
| barley | 6G | 2C,8G | 3G | 7G |
| wild oats | 5G | 7G | 3G | 5G |
| downy brome | 5G | 8G | 5G | 6G |
| cheatgrass | 6G | 8G | 5G | 7G |
| blackgrass | 5G | 1C,7G | 6G | 2C,7G |
| annual bluegrass | 6G | 1C,8G | 4G | 3C,8G |
| green foxtail | 0 | 2C,6G | 0 | 2C,5G |
| quackgrass | 4G | 8G | 2G | 6G |
| Italian ryegrass | 8G | 2C,9G | 2C,6G | 2C,8G |
| ripgut brome | 6G | 1C,8G | 5G | 7G |
| Russian thistle | 0 | 2C,5G | 0 | 10C |
| tansy mustard | 8G | 2C,9G | 5G | 8G |
| Galium aparine | 9G | 10E | 0 | 3G |
| tumble mustard | 7G | 9G | 0 | 6G |
| kochia | — | — | — | 0 |
| shepherd's purse | 2C,9G | 10C | 5G | 10C |
| *Matricaria inodora* | 8G | 9G | 3G | 9G |
| black nightshade | 0 | 5G | 0 | 4G |
| yellow rocket | 8G | 9G | 0 | 6G |
| rapeseed | 2C,8G | 9G | 7G | 9C,9G |
| wild buckwheat | 0 | 6G | 0 | 3G |

What is claimed is:
1. A compound having the formula

$$L-SO_2N=\underset{R}{\underset{|}{C}}-\underset{}{\overset{SR''}{\underset{|}{N}}}-A \qquad II$$

wherein
R is H or $CH_3$;
R'' is $C_1$-$C_3$ alkyl;
L is

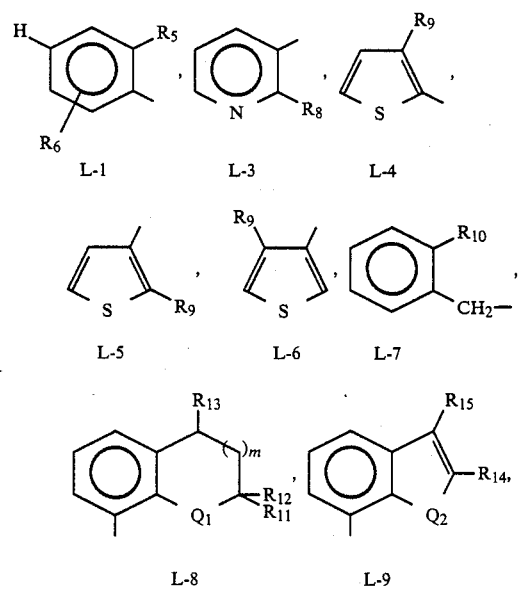

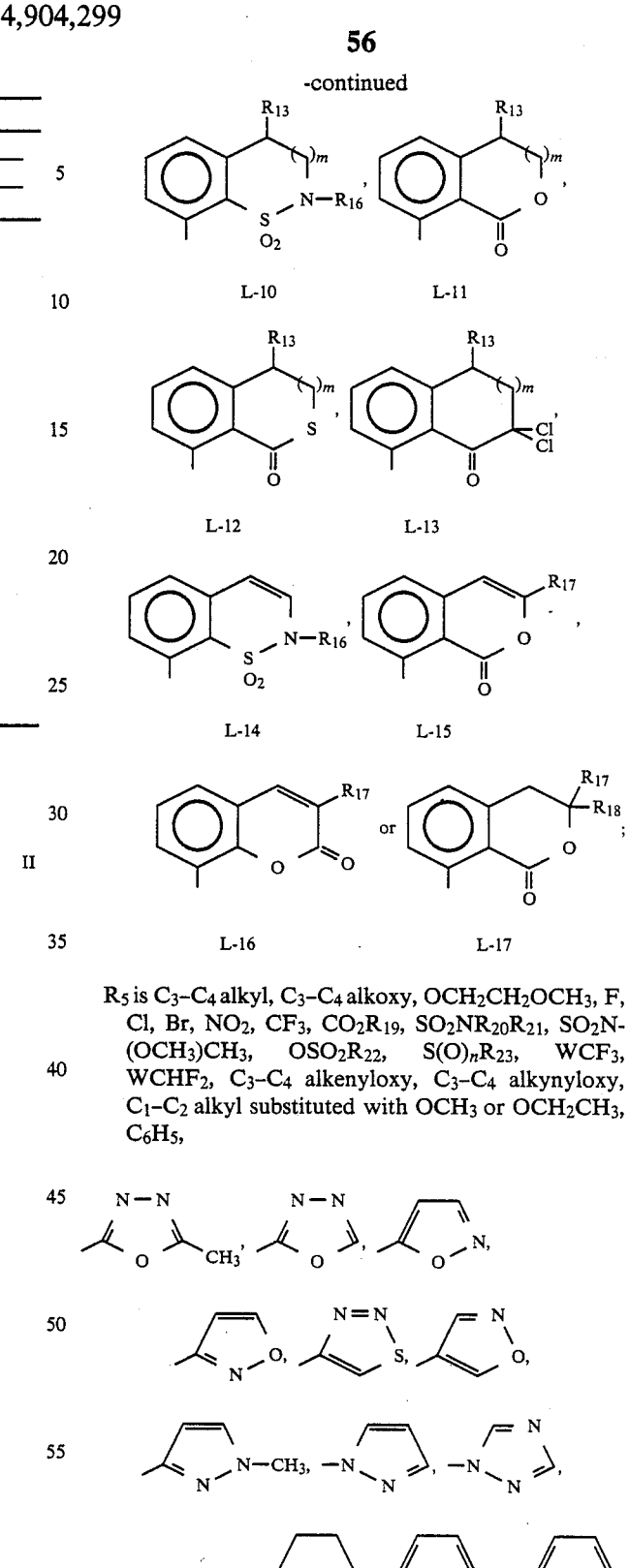

$R_5$ is $C_3$-$C_4$ alkyl, $C_3$-$C_4$ alkoxy, $OCH_2CH_2OCH_3$, F, Cl, Br, $NO_2$, $CF_3$, $CO_2R_{19}$, $SO_2NR_{20}R_{21}$, $SO_2N(OCH_3)CH_3$, $OSO_2R_{22}$, $S(O)_nR_{23}$, $WCF_3$, $WCHF_2$, $C_3$-$C_4$ alkenyloxy, $C_3$-$C_4$ alkynyloxy, $C_1$-$C_2$ alkyl substituted with $OCH_3$ or $OCH_2CH_3$, $C_6H_5$, $R_6$ is H, F, Cl, Br, $CF_3$, $CH_3$, $OCH_3$, $SCH_3$ or $OCF_2H$;
$R_8$ is $CH_3$, $CH_2CH_3$, $OCH_3$, $OCH_2CH_3$, F, Cl, Br, $SO_2NR_{20}R_{21}$, $SO_2N(OCH_3)CH_3$ or $S(O)_nR_{23}$;
$R_9$ is $C_2$-$C_3$ alkyl, F, Cl, Br, $NO_2$, $CO_2R_{19}$, $SO_2NR_{20}R_{21}$, $SO_2N(OCH_3)CH_3$ or $S(O)_nR_{23}$;

$R_{10}$ is Cl, $NO_2$, $CO_2CH_3$, $CO_2CH_2CH_3$, $SO_2N(CH_3)_2$, $OSO_2CH_3$, $SO_2CH_3$, $SO_2CH_2CH_3$, $OCH_3$ or $OCH_2CH_3$;

$R_{11}$ is H, $CH_3$ or $CH_2CH_3$;

$R_{12}$ is H, $CH_3$ or $CH_2CH_3$;

$R_{13}$ is H or $CH_3$;

$R_{14}$ is H or $CH_3$;

$R_{15}$ is H or $CH_3$;

$R_{16}$ is $CH_3$ or $CH_2CH_3$;

$R_{17}$ is H or $C_1-C_4$ alkyl;

$R_{18}$ is H or $CH_3$;

$R_{19}$ is $C_1-C_4$ alkyl, $CH_2CH_2OCH_3$, $CH_2CH_2Cl$ or $CH_2CH=CH_2$;

$R_{20}$ is $C_1-C_3$ alkyl;

$R_{21}$ is $C_1-C_3$ alkyl;

$R_{22}$ is $C_1-C_3$ alkyl or $N(CH_3)_2$;

$R_{23}$ is $C_1-C_3$ alkyl or $CH_2CH=CH_2$;

m is 0 or 1;

n is 0 or 2;

$Q_1$ is O, S, $SO_2$ or $NR_{17}$;

$Q_2$ is O, S or $NR_{17}$; and

W is O, S or $SO_2$;

A is

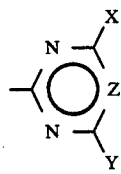 A-1

X is $CH_3$, $OCH_3$, $OCH_2CH_3$, Cl, F, Br, $OCF_2H$, $CH_2F$ or $CF_3$;

Y is H, $CH_3$, $OCH_3$, $OCH_2CH_3$, $CH_2OCH_3$, $CH_2OCH_2CH_3$, $N(CH_3)_2$, $CH_2CH_3$, $CF_3$, $SCH_3$, $OCH_2CH=CH_2$, $OCH_2C\equiv CH$, $OCH_2CF_3$, $OCH_2CH_2OCH_3$, $CH_2SCH_3$, $OCF_2H$, $SCF_2H$, $CR_{24}(QCH_3)_2$,

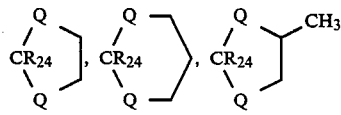

or $CR_{24}(QCH_2CH_3)_2$;

Q is O or S;

$R_{24}$ is H or $CH_3$;

Z is CH;

provided that (1) the total number of carbon atoms of $R_{20}$ and $R_{21}$ is less than or equal to four;

(2) when m is 1, then $R_{13}$ is H;

(3) when L is L-17, then $R_{17}$ and $R_{18}$ are not simultaneously H;

(4) when X is Cl, F or Br, then Z is CH and Y is $OCH_3$, $OCH_2CH_3$, $N(CH_3)_2$ or $OCF_2H$;

(5) when X or Y is $OCF_2H$, then Z is CH;

provided that (1) when L is L-1, then $R_5$ is $C_2-C_4$ alkyl, $C_2-C_4$ alkoxy, $OCH_2CH_2OCH_3$, $OSO_2R_{22}$, $S(O)_nCH_2CH=CH_2$, $WCF_2$, $WCHF_2$, $C_3-C_4$ alkenyloxy, $C_3-C_4$ alkynyloxy, $C_1-C_2$ alkyl substituted with $OCH_3$ or $OCH_2CH_3$,

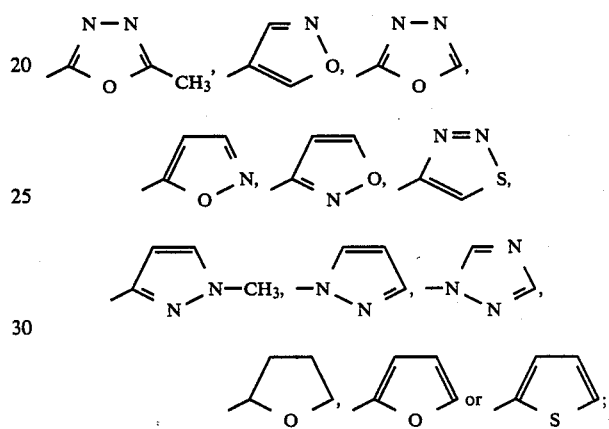

(2) when L is L-3, then $R_8$ is $SO_2NR_{20}R_{21}$, $SO_2N(OCH_3)CH_3$ or $SO_2R_{23}$;

(3) when L is L-4, L-5 or L-6, then $R_9$ is $C_1-C_3$ alkyl, F, Cl, Br, $NO_2$, $SO_2NR_{20}R_{21}$, $SO_2N(OCH_3)CH_3$ or $S(O)_nR_{23}$.

2. A compound of claim 1 wherein R is H.

3. A composition suitable for controlling the growth of undesired vegetation which comprises a herbicidally effective amount of a compound of claim 1 and at least one of the following: surfactant, solid or liquid diluent.

4. A method for the control of undesired vegetation which comprises applying to the locus of the undesired vegetation a herbicidally effective amount of a compound of claim 1.

* * * * *